United States Patent
Muller et al.

(10) Patent No.: US 11,478,628 B2
(45) Date of Patent: Oct. 25, 2022

(54) HEART PUMP PROVIDING ADJUSTABLE OUTFLOW

(71) Applicant: TC1 LLC, Pleasanton, CA (US)

(72) Inventors: Paul F. Muller, San Carlos, CA (US); Keif M. Fitzgerald, San Jose, CA (US)

(73) Assignee: TC1 LLC, St. Paul, MN (US)

( * ) Notice: Subject to any disclaimer, the term of this patent is extended or adjusted under 35 U.S.C. 154(b) by 254 days.

(21) Appl. No.: 16/442,106

(22) Filed: Jun. 14, 2019

(65) Prior Publication Data

US 2019/0365975 A1 Dec. 5, 2019

Related U.S. Application Data

(63) Continuation of application No. 15/303,698, filed as application No. PCT/US2015/026014 on Apr. 15, 2015, now Pat. No. 10,363,349.

(Continued)

(51) Int. Cl.
| | | |
|---|---|---|
| *A61M 60/205* | (2021.01) | |
| *A61M 60/50* | (2021.01) | |
| *A61M 60/824* | (2021.01) | |
| *A61M 60/829* | (2021.01) | |
| *A61M 60/857* | (2021.01) | |
| *A61M 60/135* | (2021.01) | |
| *A61M 60/148* | (2021.01) | |

(Continued)

(52) U.S. Cl.
CPC .......... *A61M 60/50* (2021.01); *A61M 60/205* (2021.01); *A61M 60/824* (2021.01); *A61M 60/829* (2021.01); *A61M 60/857* (2021.01); *A61M 60/135* (2021.01); *A61M 60/148* (2021.01); *A61M 60/414* (2021.01); *A61M 60/818* (2021.01); *A61M 2205/3334* (2013.01)

(58) Field of Classification Search
CPC .. A61M 60/50; A61M 60/829; A61M 60/824; A61M 60/857; A61M 60/205; A61M 60/148; A61M 60/414; A61M 60/135; A61M 60/818; A61M 2205/3334
USPC ..................................... 600/15–18
See application file for complete search history.

(56) References Cited

U.S. PATENT DOCUMENTS

| | | |
|---|---|---|
| 3,995,617 A | 12/1976 | Watkins et al. |
| 4,560,375 A | 12/1985 | Schulte et al. |

(Continued)

FOREIGN PATENT DOCUMENTS

| | | | |
|---|---|---|---|
| CA | 2292432 A1 * | 12/1998 | .......... A61M 60/205 |
| WO | 2002070039 A2 | 9/2002 | |
| WO | 2013167432 A1 | 11/2013 | |

OTHER PUBLICATIONS

Abiomed, "Impella 5.0 with the Impella Console, Circulatory Support System, Instructions for Use & Clinical Reference Manual," Jun. 2010, in 122 pages.

*Primary Examiner* — Carl H Layno
*Assistant Examiner* — Michael J Lau
(74) *Attorney, Agent, or Firm* — Armstrong Teasdale LLP

(57) ABSTRACT

A heart pump is disclosed herein. The heart pump can include a cannula having one or more outlets. An impeller can be positioned in the cannula. The impeller can be configured to pump blood through the outlets along a longitudinal axis when the impeller is rotated at an operational speed. The heart pump can be configured to adjust an effective area of the outlets while the impeller is rotating or to provide relative motion between the cannula and the impeller along the longitudinal axis while the impeller is rotating.

20 Claims, 26 Drawing Sheets

Related U.S. Application Data

(60) Provisional application No. 61/979,925, filed on Apr. 15, 2014.

(51) Int. Cl.
*A61M 60/414* (2021.01)
*A61M 60/818* (2021.01)

(56) References Cited

U.S. PATENT DOCUMENTS

| | | | |
|---|---|---|---|
| 4,752,183 A * | 6/1988 | Sakurai | F04D 15/0038 415/12 |
| 4,817,586 A | 4/1989 | Wampler | |
| 4,900,227 A | 2/1990 | Trouplin | |
| 4,976,270 A | 12/1990 | Pari et al. | |
| 5,055,005 A * | 10/1991 | Kletschka | F04D 29/426 417/356 |
| 5,092,844 A | 3/1992 | Schwartz et al. | |
| 5,190,528 A | 3/1993 | Fonger et al. | |
| 5,307,288 A * | 4/1994 | Haines | G01F 1/363 700/282 |
| 5,314,406 A * | 5/1994 | Arias | A61M 3/0233 604/21 |
| 5,755,784 A | 5/1998 | Jarvik | |
| 5,807,311 A | 9/1998 | Palestrant | |
| 5,888,242 A | 3/1999 | Antaki et al. | |
| 5,947,892 A * | 9/1999 | Benkowski | A61M 60/00 600/16 |
| 6,086,527 A | 7/2000 | Talpade | |
| 6,132,363 A | 10/2000 | Freed et al. | |
| 6,135,943 A | 10/2000 | Yu et al. | |
| 6,152,704 A | 11/2000 | Aboul-Hosn et al. | |
| 6,190,357 B1 | 2/2001 | Ferrari et al. | |
| 6,210,318 B1 | 4/2001 | Lederman | |
| 6,217,541 B1 | 4/2001 | Yu | |
| 6,234,995 B1 | 5/2001 | Peacock, III | |
| 6,245,007 B1 * | 6/2001 | Bedingham | A61M 60/829 600/16 |
| 6,413,222 B1 | 7/2002 | Pantages et al. | |
| 6,422,990 B1 | 7/2002 | Prem | |
| 6,645,241 B1 | 11/2003 | Strecker | |
| 6,776,794 B1 | 8/2004 | Hong et al. | |
| 6,981,942 B2 | 1/2006 | Khaw et al. | |
| 7,011,620 B1 * | 3/2006 | Siess | H02K 7/083 600/16 |
| 7,241,257 B1 | 7/2007 | Ainsworth et al. | |
| 7,828,710 B2 | 11/2010 | Shifflette | |
| 7,841,976 B2 * | 11/2010 | McBride | F04D 29/181 600/16 |
| 7,927,068 B2 | 4/2011 | McBride et al. | |
| 8,632,449 B2 * | 1/2014 | Masuzawa | F04D 29/048 600/17 |
| 8,668,473 B2 * | 3/2014 | LaRose | A61M 60/422 417/356 |
| 8,992,406 B2 * | 3/2015 | Corbett | A61M 60/135 600/16 |
| 9,364,593 B2 * | 6/2016 | McBride | F04D 29/528 |
| 2004/0000442 A1 | 3/2004 | Siess | |
| 2004/0044266 A1 * | 3/2004 | Siess | A61M 25/0662 600/16 |
| 2005/0001313 A1 | 6/2005 | Bolling | |
| 2005/0131385 A1 * | 6/2005 | Bolling | A61M 25/003 604/509 |
| 2006/0001551 A1 | 7/2006 | Aboul-Hosn | |
| 2006/0001987 A1 | 9/2006 | Thut | |
| 2006/0198725 A1 * | 9/2006 | Thut | F04D 7/065 415/93 |
| 2008/0114339 A1 * | 5/2008 | McBride | F04D 3/02 604/891.1 |
| 2008/0001327 A1 | 6/2008 | Shifflete | |
| 2008/0199357 A1 * | 8/2008 | Gellman | A61M 1/1698 422/48 |
| 2010/0002108 A1 | 8/2010 | Aboul-Hosn | |
| 2010/0210895 A1 | 8/2010 | Aboul-Hosn et al. | |
| 2011/0000040 A1 | 1/2011 | Campbell | |
| 2011/0004046 A1 * | 1/2011 | Campbell | A61M 60/135 600/16 |
| 2012/0000354 A1 | 2/2012 | LaRose | |
| 2012/0035411 A1 * | 2/2012 | LaRose | A61M 60/419 600/16 |
| 2012/0001726 A1 | 7/2012 | Bates | |
| 2012/0001789 A1 | 7/2012 | Campbell et al. | |
| 2012/0178986 A1 * | 7/2012 | Campbell | A61M 60/857 600/16 |
| 2012/0002456 A1 | 9/2012 | Masuzawa | |
| 2012/0245680 A1 * | 9/2012 | Masuzawa | F04D 29/042 623/3.11 |
| 2013/0000536 A1 | 2/2013 | Corbett | |
| 2013/0001382 A1 | 5/2013 | Kushwaha et al. | |
| 2013/0002092 A1 | 8/2013 | Baykut et al. | |
| 2013/0280692 A1 * | 10/2013 | Gourlay | A61M 1/32 435/1.2 |
| 2013/0003038 A1 | 11/2013 | Evans | |
| 2013/0303831 A1 * | 11/2013 | Evans | A61M 1/101 600/16 |
| 2013/0003316 A1 | 12/2013 | Campbell et al. | |
| 2014/0000106 A1 | 1/2014 | Tanner et al. | |
| 2014/0002883 A1 | 9/2014 | Timms | |
| 2014/0288354 A1 * | 9/2014 | Timms | A61M 1/3659 600/16 |
| 2016/0354525 A1 * | 12/2016 | McBride | A61M 60/148 |
| 2017/0000796 A1 | 3/2017 | Mohajer-Shojaee | |
| 2017/0079639 A1 * | 3/2017 | Mohajer-Shojaee | A61B 17/0482 |

\* cited by examiner

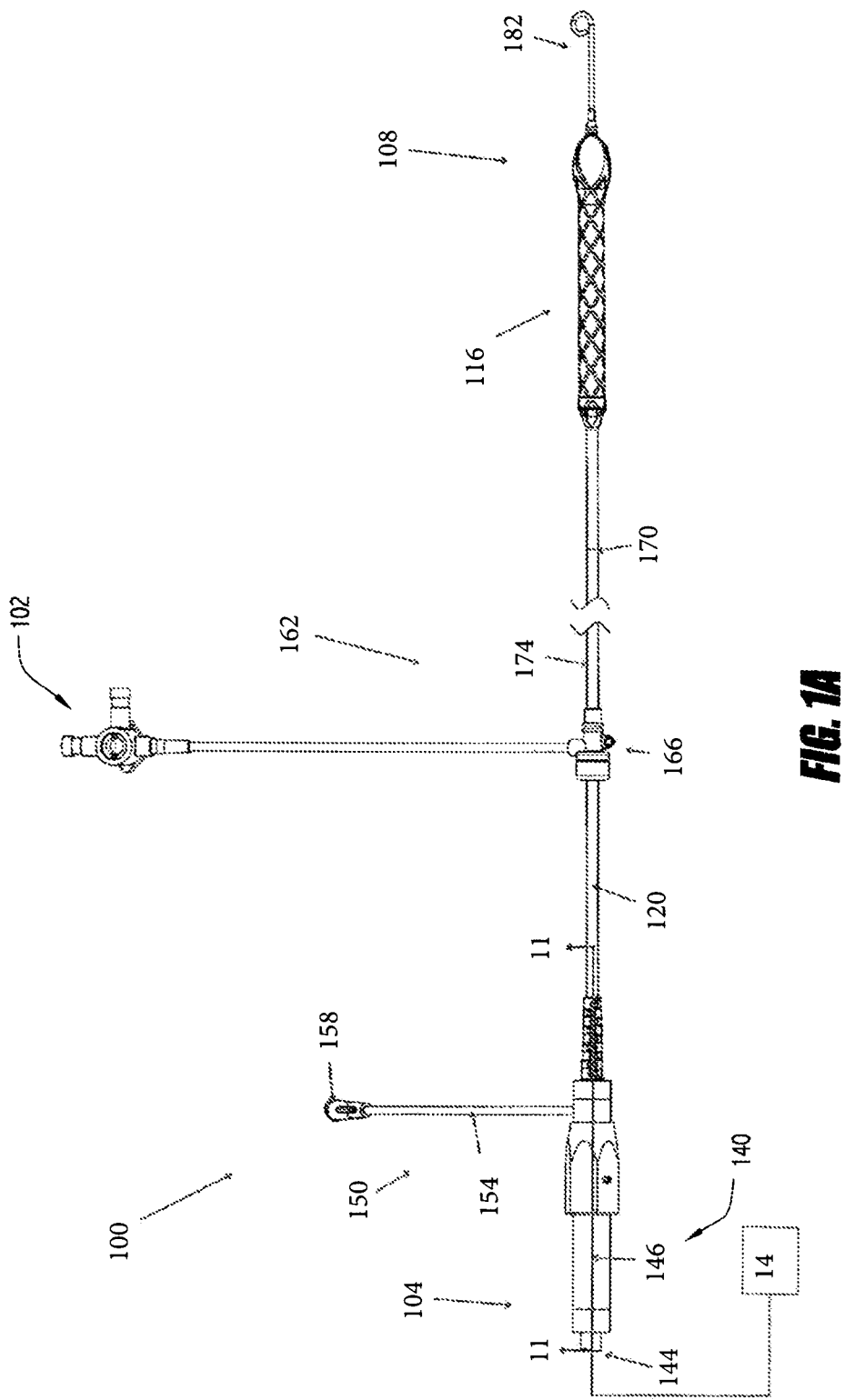

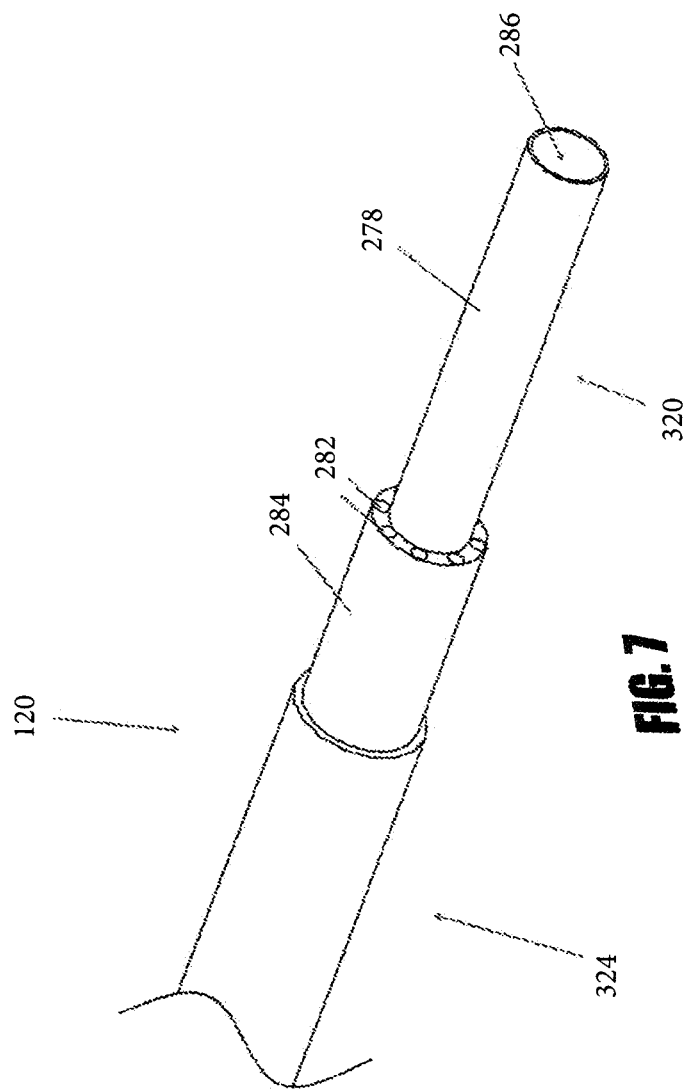

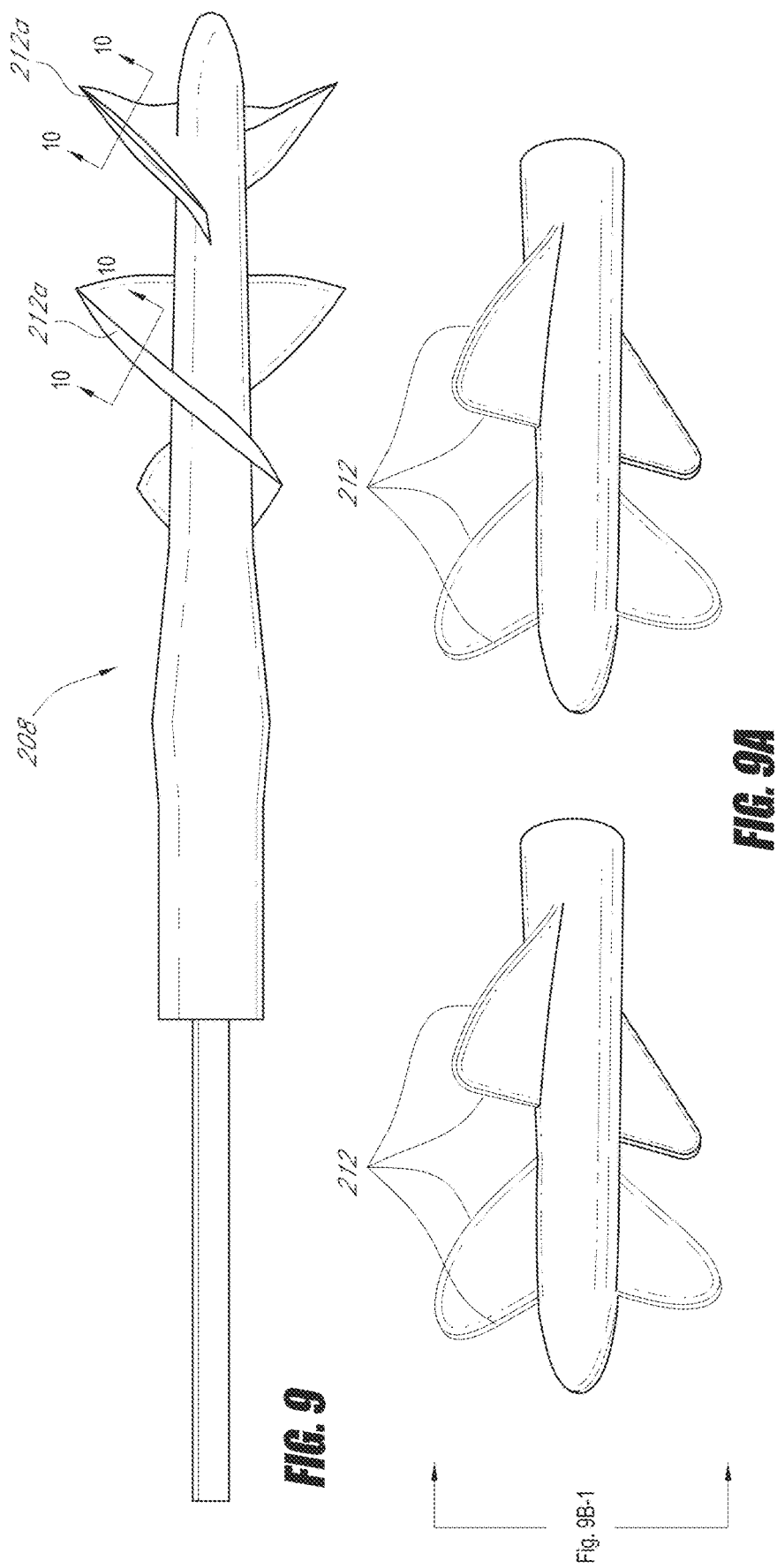

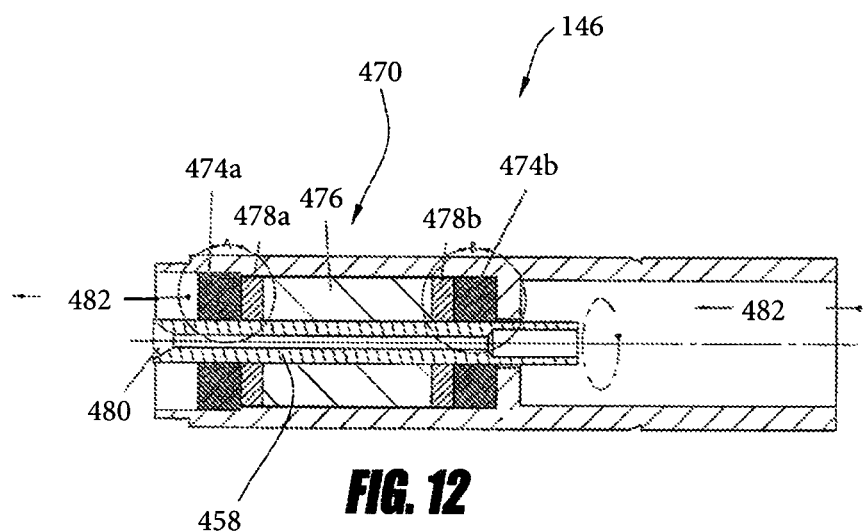
FIG. 12
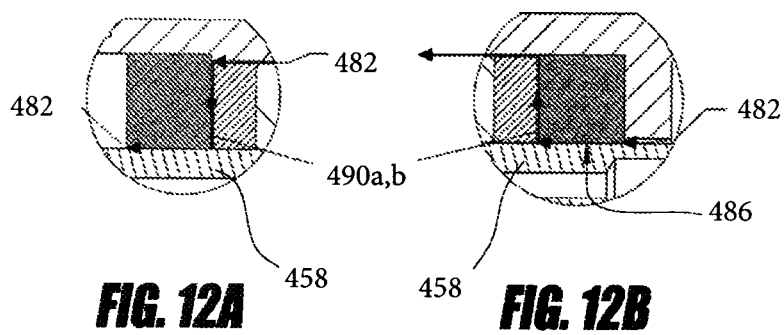
FIG. 12A  FIG. 12B

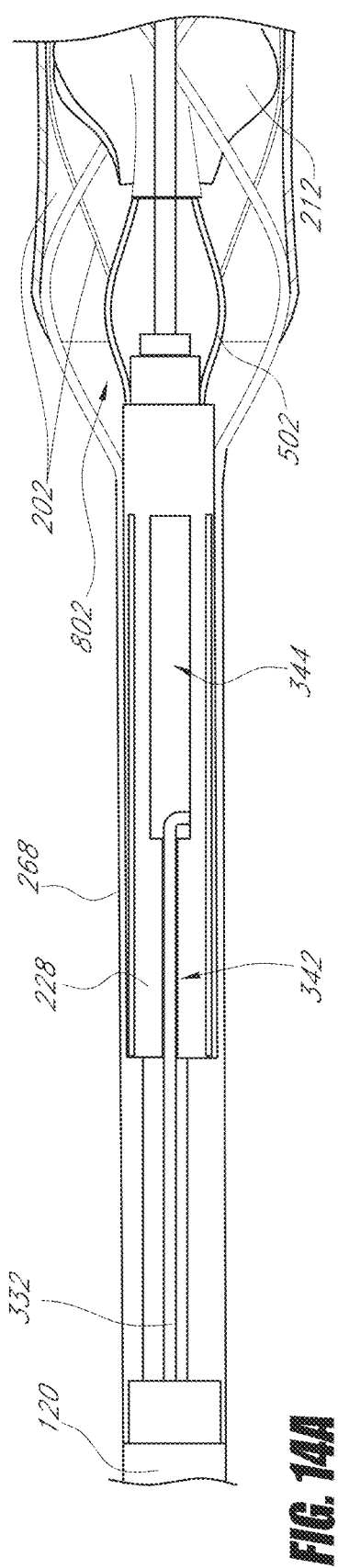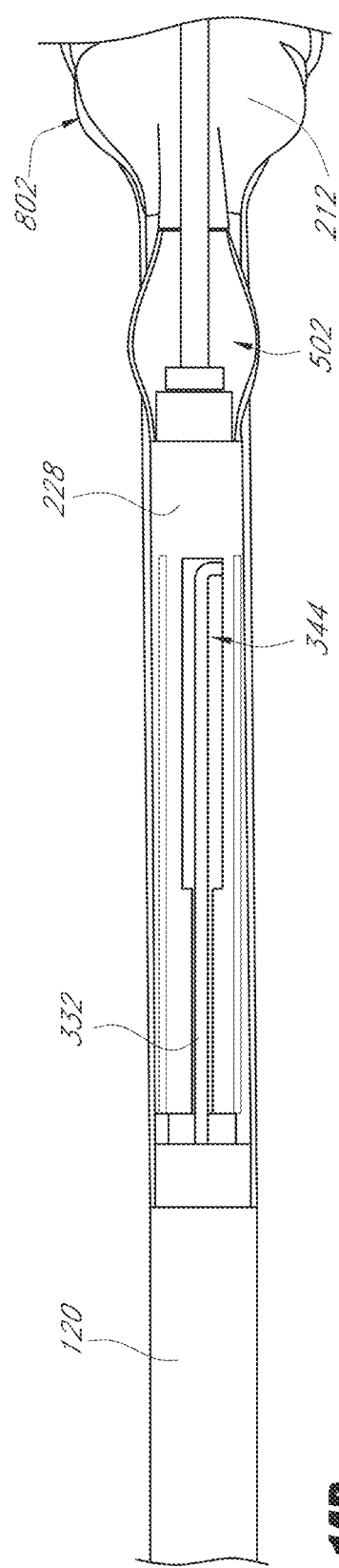
FIG. 14A
FIG. 14B

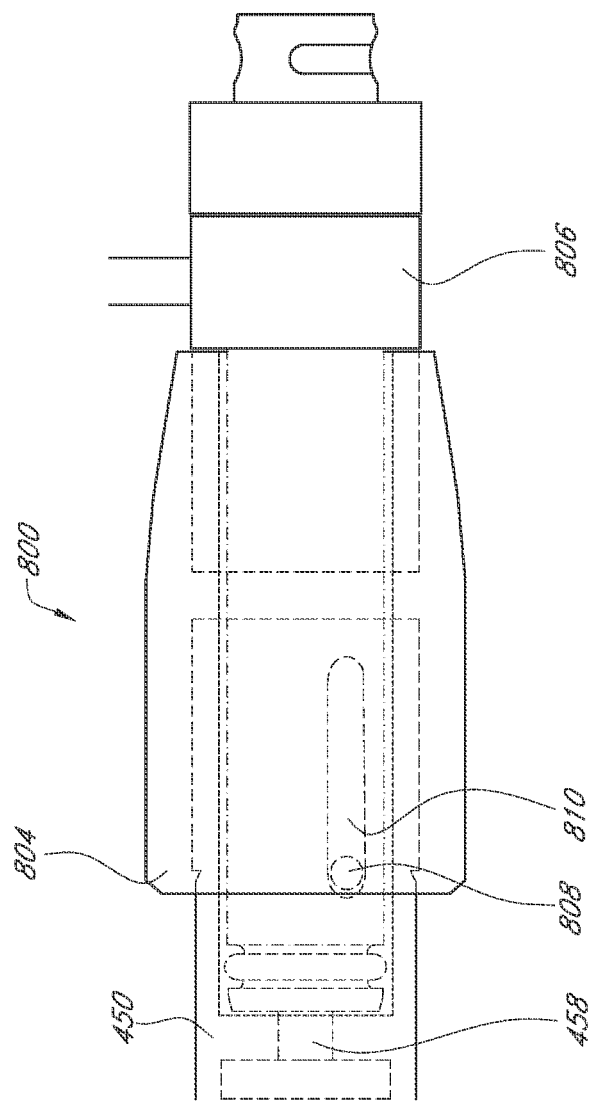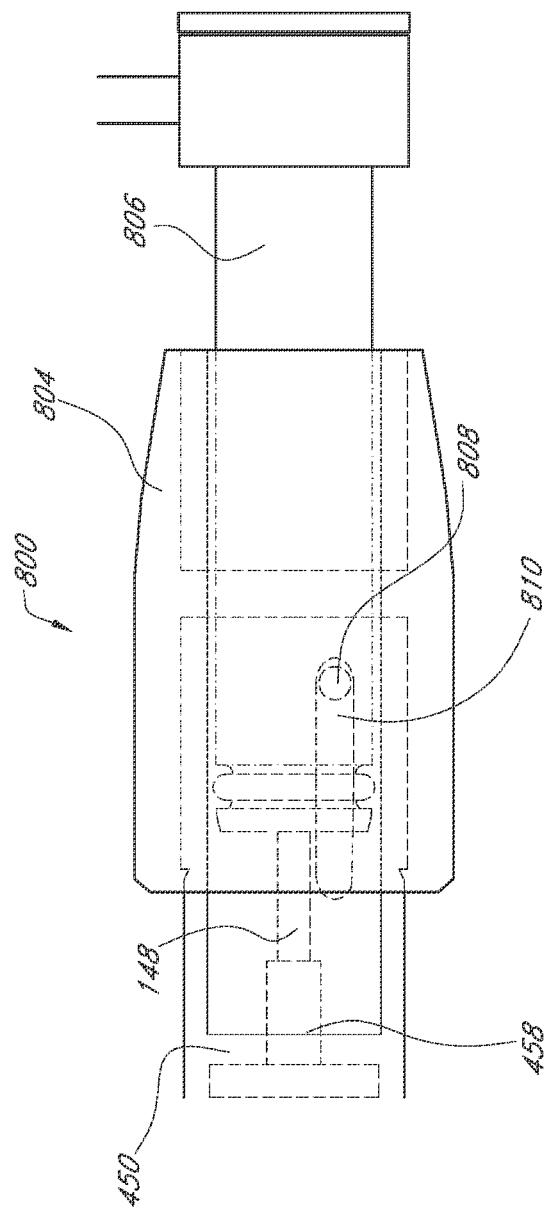

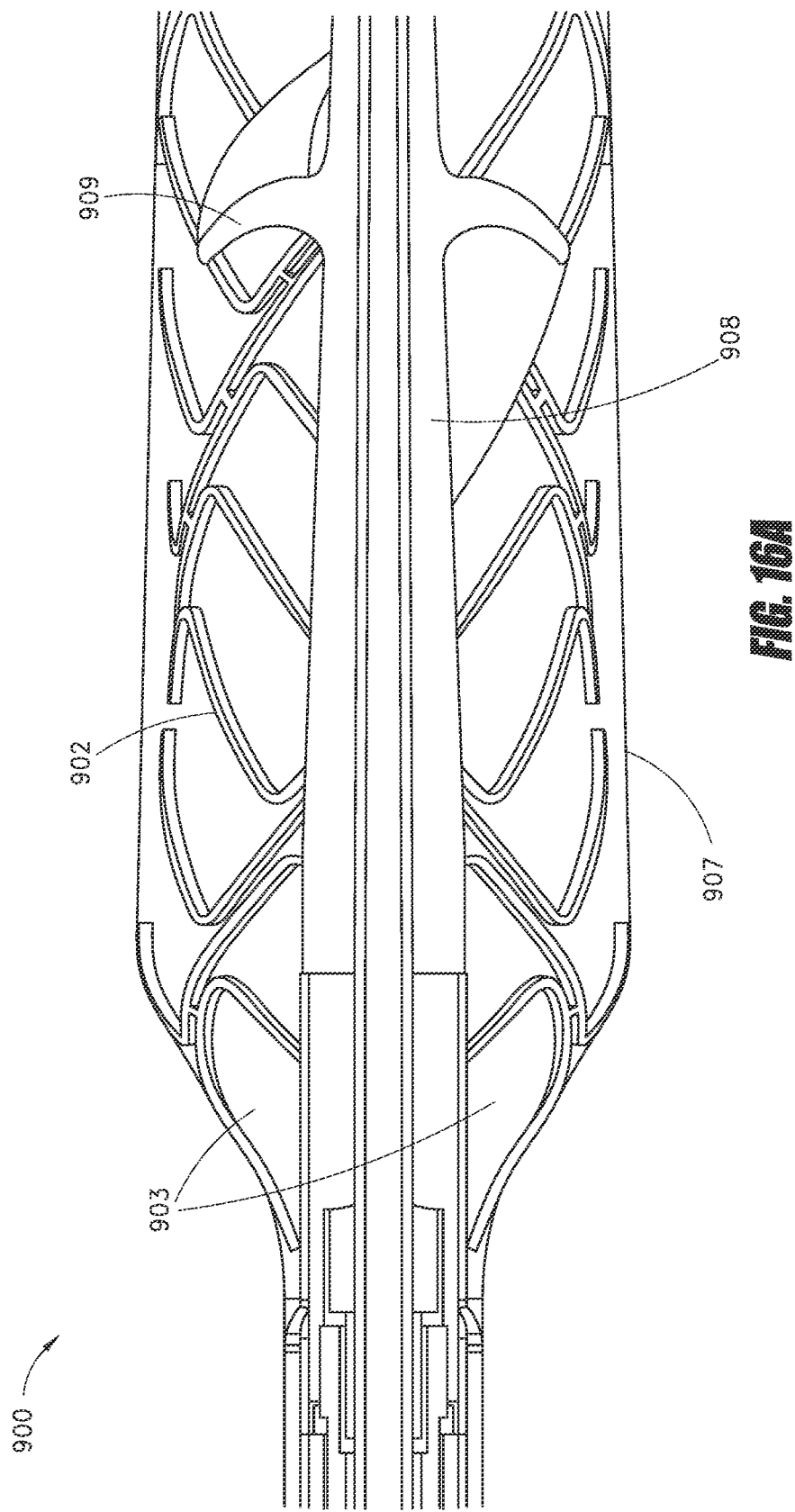

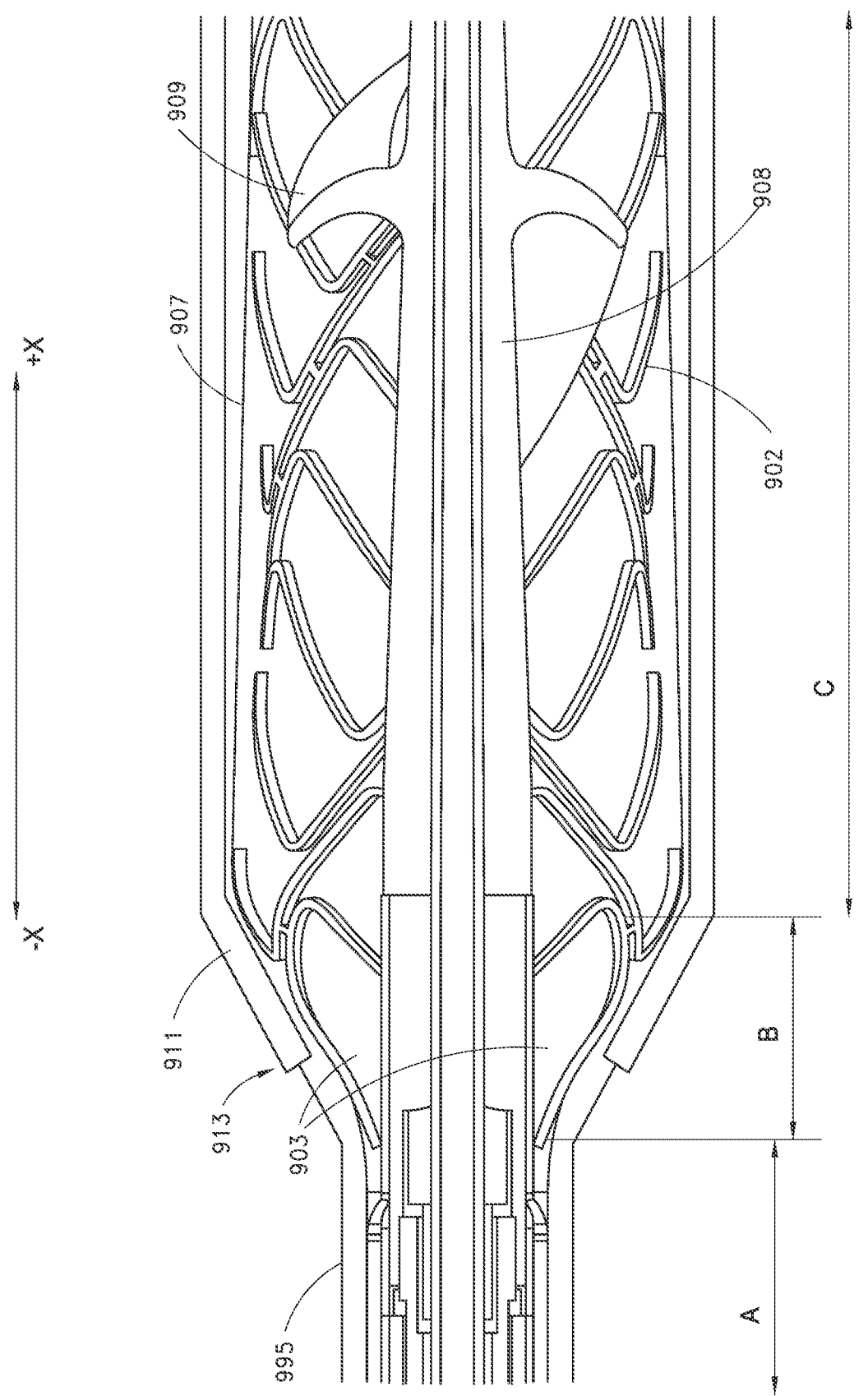

HEART PUMP PROVIDING ADJUSTABLE OUTFLOW

CROSS-REFERENCE TO RELATED APPLICATIONS

This application is a Continuation of U.S. patent application Ser. No. 15/303,698 filed on Oct. 10, 2016, now U.S. patent Ser. No. 10/363,349; which is a National Stage Application claiming priority to International Application No. PCT/US15/26014 filed on Apr. 15, 2015, which claims the benefit of priority to U.S. Provisional Patent Application No. 61/979,925, filed Apr. 15, 2014, the contents of which are incorporated by reference herein in their entirety and for all purposes.

BACKGROUND OF THE INVENTION

Field of the Invention

This application is directed to heart pumps that can be applied percutaneously.

Description of the Related Art

Heart disease is a major health problem that claims many lives per year. After a heart attack, only a small number of patients can be treated with medicines or other non-invasive treatment. However, a significant number of patients can recover from a heart attack or cardiogenic shock if provided with mechanical circulatory support.

In a conventional approach, a blood pump having a fixed cross-section is surgically inserted a heart chamber, such as into the left ventricle of the heart and the aortic arch to assist the pumping function of the heart. Other known applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. Surgical insertion, however, can cause additional serious stresses in heart failure patients.

Percutaneous insertion of a left ventricular assist device ("LVAD"), a right ventricular assist device ("RVAD") or in some cases a system for both sides of the heart (sometimes called "biVAD") therefore is desired. Conventional fixed cross-section ventricular assist devices designed to provide near full heart flow rate are too large to be advanced percutaneously, e.g., through the femoral artery. There is an urgent need for a pumping device that can be inserted percutaneous and also provide full cardiac rate flows of the left, right, or both the left and right sides of the heart when called for.

SUMMARY OF THE INVENTION

In one embodiment, a heart pump is disclosed. The heart pump can include a cannula having one or more outlets. An impeller can be positioned in the cannula. The impeller can be configured to pump blood through the outlets along a longitudinal axis when the impeller is rotated at an operational speed. The heart pump can be configured to adjust an effective area of the outlets while the impeller is rotating or to provide relative motion between the cannula and the impeller along the longitudinal axis while the impeller is rotating.

In another embodiment, a method of operating a heart pump is disclosed. The method can comprise advancing a cannula and an impeller to a target location in a patient, the impeller being positioned in the cannula. The method can include activating the heart pump to rotate the impeller to pump blood through the cannula along a longitudinal axis. The method can comprise providing relative motion between the impeller and the cannula along the longitudinal axis while the impeller is rotating.

In yet another embodiment, a method of operating a heart pump is disclosed. The method can comprise advancing a cannula and an impeller to a target location in a patient, the impeller being positioned in the cannula. The cannula can comprise one or more outlets. The method can include activating the heart pump to rotate the impeller to pump blood through the cannula along a longitudinal axis. The method can include adjusting an effective area of the outlets while the impeller is rotating.

In one embodiment, a heart pump is provided that includes a catheter body, a housing, an impeller, and a diffuser. The catheter body includes a proximal end, a distal end, and an elongate body extending therebetween. The housing is coupled with the distal end of the catheter body and comprises a distal opening and a proximal opening. The impeller assembly is coupled with the distal end of the catheter body and positioned within the housing. The diffuser can include a flow directing surface. The diffuser is disposed between the distal end of the catheter body and the impeller. The diffuser is configured to be positioned within the housing and adjacent the proximal opening.

In another embodiment, a heart pump is provided that includes a catheter body comprising a proximal end, a distal end, and an elongate body extending therebetween. The pump also includes an impeller coupled with the distal end of the catheter body and comprising an axial lumen passing through a distal end of the impeller. The impeller comprises a tip positioned at the distal end of the impeller, the tip comprising a resealable member having a resealable path.

In another embodiment, a heart pump is provided that comprises a catheter body, an impeller, and a sheath. The catheter body has a proximal end, a distal end, and an elongate structure extending therebetween. The impeller is coupled with the distal end of the catheter body. The sheath is disposed over at least a portion of the distal end of the catheter body. The sheath also has an expandable distal end.

In another embodiment, a catheter assembly is provided that includes a catheter body, an impeller, and a deployment device. The catheter body comprises a proximal end, a distal end, and an elongate structure extending therebetween. The impeller is configured for relative motion in an axial direction, and is located at the distal end of the catheter body. The deployment device is located at the proximal end of the catheter assembly.

BRIEF DESCRIPTION OF THE DRAWINGS

A more complete appreciation of the subject matter of the present inventions and the various advantages thereof can be realized by reference to the following detailed description, in which reference is made to the accompanying drawings in which:

FIG. 1A is a plan view of one embodiment of a catheter assembly adapted to be used with the heart pump of FIG. 1;

FIG. 7 is a perspective view of one embodiment of a catheter body that can be used to house a drive shaft and to convey an infusant to the bearing housing of FIG. 5;

FIG. 9 illustrates one embodiment of an impeller assembly;

FIGS. 9A, 9B-1, 9B-2, 10 and 10A illustrate details of further embodiments of impeller blades;

FIGS. 12, 12A, and 12B are cross-section views similar to that of FIG. 11, illustrating an infusant outflow path;

FIGS. 14A-B are partial cross-sectional views illustrating one embodiment of a blood pump including a retractable impeller assembly in deployed and retracted configurations, respectively;

FIGS. 15A-B illustrate a deployment device disposed at the proximal end of a catheter assembly illustrated in FIGS. 14A-B in deployed and retracted configurations, respectively;

FIGS. 16A-16B are side cross-sectional views of a catheter pump having a cannula and an impeller disposed within the cannula, according to some embodiments;

FIG. 17 is a side cross-sectional view of a catheter pump, according to another embodiment.

DETAILED DESCRIPTION

Figure 1:
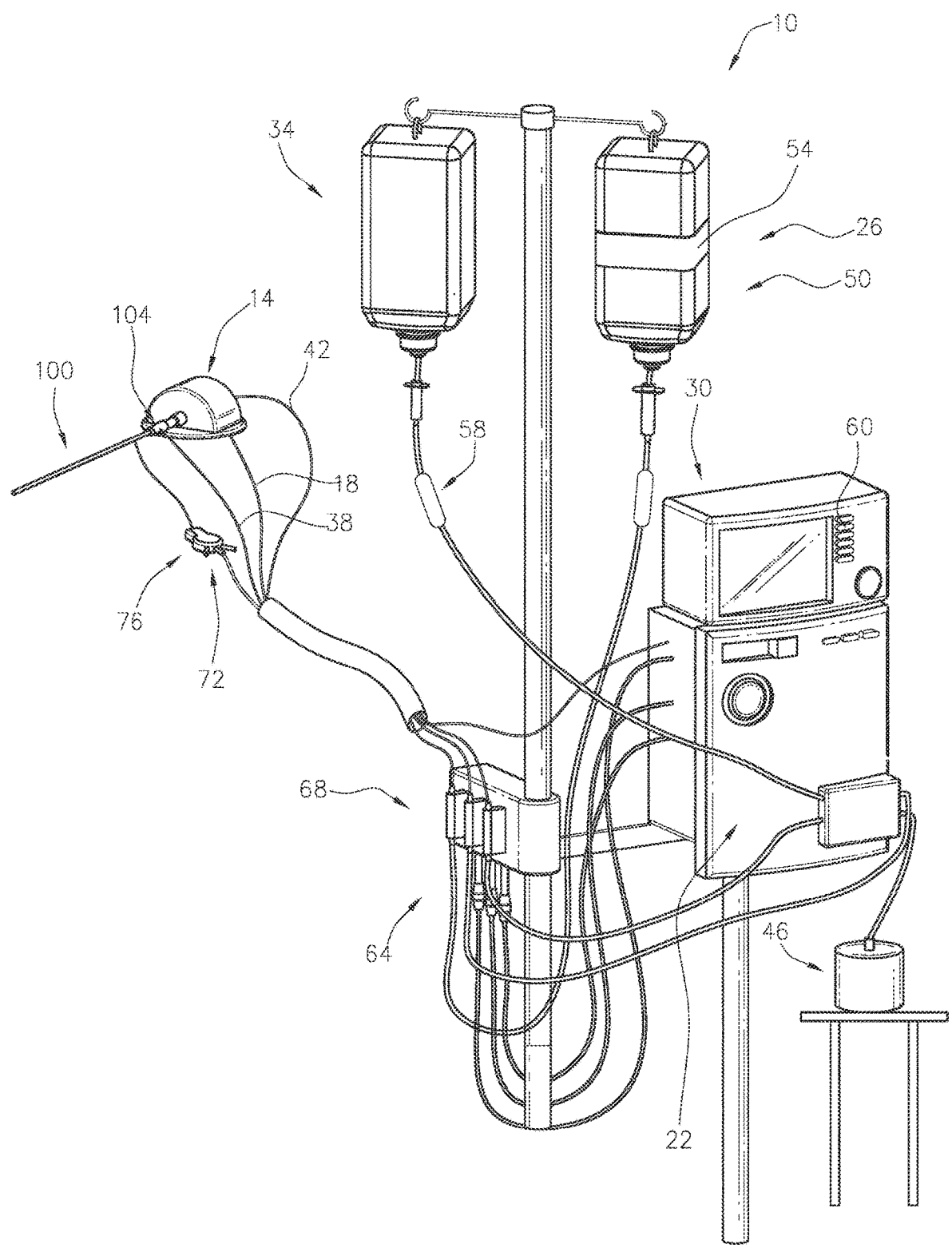
FIG. 1 illustrates one embodiment of a heart pump configured for percutaneous application and operation.

Major components of heart pumps that can be applied percutaneously to a patient are described below in Section I. Section II describes various structures that facilitate the rotatable support of a cantilevered impeller. Section III describes various structures that facilitate deployment and/or retrieval of one or more components of the distal end 108 of the heart pump 10 within the cardiovascular system. Section IV describes various methods and techniques in connection with specific structures of heart pumps I. Overview of Heart Pumps FIG. 1 illustrates one embodiment of a heart pump 10 that includes a catheter assembly 100 having a proximal end 104 adapted to connect to a motor 14 and a distal end 108 (see FIG. 1A) adapted to be inserted percutaneously into a patient. The motor 14 is connected by a signal line 18 to a control module 22 that provides power and/or control signals to the motor 14. As discussed further below, the heart pump 10 in various embodiments has an infusion system 26 and a patient monitoring system 30.

The infusion system 26 can provide a number of benefits to the heart pump 10 which are discussed below. In one embodiment, the infusion system 26 includes a source of infusant 34, a fluid conduit 38 extending from the infusant source 34 to the proximal end 104 of the catheter assembly 100 and a fluid conduit 42 extending from the proximal end of the catheter assembly 100 to a waste container 46. The flow of infusant to and from the catheter assembly 100 can be by any means, including a gravity system or one or more pumps. In the illustrated embodiment, the infusant source 34 includes an elevated container 50, which may be saline or another infusant as discussed below. Flow from the elevated container 50 can be regulated by a pressure cuff 54 to elevate the pressure of the fluid in the container 50 to increase flow or by a pinch valve 58 or by other means.

The patient monitoring system 30 can be used to monitor the operation of the patient and/or the pump 10. For example, the patient monitoring system 30 can include a user interface 60 coupled with a source of data 64. The data source 64 can include one or more patient conditions sensors, such as pressure sensors 68 that are in pressure communication with the patient and/or operating components within the patient. In one embodiment, the pressure sensors 68 fluidly communicate by a conduit 72 that extends between the sensors and a proximal portion of the catheter assembly 100. The conduit 72 can include a plurality of separable segments and can include a valve 76 to enable or disable the pressure communication to the sensors 68.

The heart pump 10 is adapted to provide an acute or other short-term treatment. A short-term treatment can be for less than a day or up to several days or weeks in some cases. With certain configurations the pump 10 can be used for a month or more.

The catheter assembly 100 extends between the proximal end 104 and the distal end 108. An impeller assembly 116 disposed at the distal end 108 is configured to pump blood to convey blood from one body cavity to another. In one arrangement, the impeller assembly 116 conveys blood proximally through or along a portion of the catheter assembly 100 to provide assistance to the left ventricle of the heart. In another embodiment, the impeller assembly 116 conveys blood distally through or along a portion of the catheter assembly 100 to provide assistance to the right ventricle of the heart. The heart pump 10 is useful as a heart assist device for treating patients with acute heart failure or other heart maladies. The heart pump 10 also can be used in connection with a surgical treatment to support the patient without providing full cardiovascular bypass. A patient could be supported on the device for longer term with proper controls and design.

The catheter assembly 100 is provided with a low profile configuration for percutaneous insertion. For example, the distal end 108 of the catheter assembly 100 can be configured to have about an 11 French (approximately 3.5 mm) size in a first configuration for insertion and an expanded configuration, such as up to about 21 French (approximately 7 mm), once positioned in the body. The larger size facilitates greater flow rates by the impeller assembly 116 as discussed below.

The catheter assembly 100 is configured to enable the distal end 108 to reach a heart chamber after being inserted initially into a peripheral vessel. For example, the catheter assembly 100 can have a suitable length to reach the left ventricle and sufficient pushability and torquability to traverse the intervening vasculature. The catheter assembly 100 may includes a multilumen catheter body 120 that is arranged to facilitate delivery and operation of the impeller assembly 116. Further details concerning various embodiments of the catheter body 120 are discussed below in connection with FIGS. 7-7C.

A drive system is provided to drive an impeller within the impeller assembly 116. The drive system includes a motor 14 and a suitably configured drive controller (not shown) disposed within the control module 22. The motor 14 is in various embodiments is configured to be disposed outside the patient, e.g., adjacent to the proximal end 104 of the catheter assembly 100. In one advantageous embodiment, the drive system employs a magnetic drive arrangement. The motor 14 is arranged to generate magnetic fields that will be sensed by permanent magnets disposed within the proximal end 104 of the catheter assembly 100. This arrangement facilitates very efficient generation of torque used to drive the impeller assembly 116, as discussed below.

Some embodiments described herein could be incorporated into a system in which a motor is miniaturized sufficiently to be inserted into the patient in use, including into the vasculature. Such an embodiment could be operated by disposing control signal lines within the proximal portion of the catheter body 120. Also, it may be useful to provide the capability to measure blood pressure at the distal end 108 using a device disposed at the proximal end 104. For example, a pressure sensor at the distal end can communicate with a device outside the patient through a lumen of the catheter body 120. Various details of these optional features are described in U.S. Pat. No. 7,070,555, which is incorporated by reference herein for all purposes and in its entirety.

In another embodiment, a mechanical interface can be provided between the motor and the proximal end 104 of the catheter assembly 100. The mechanical interface can be between the motor 14 and a drive shaft positioned at the proximal end of the catheter assembly 100.

Figure 11:
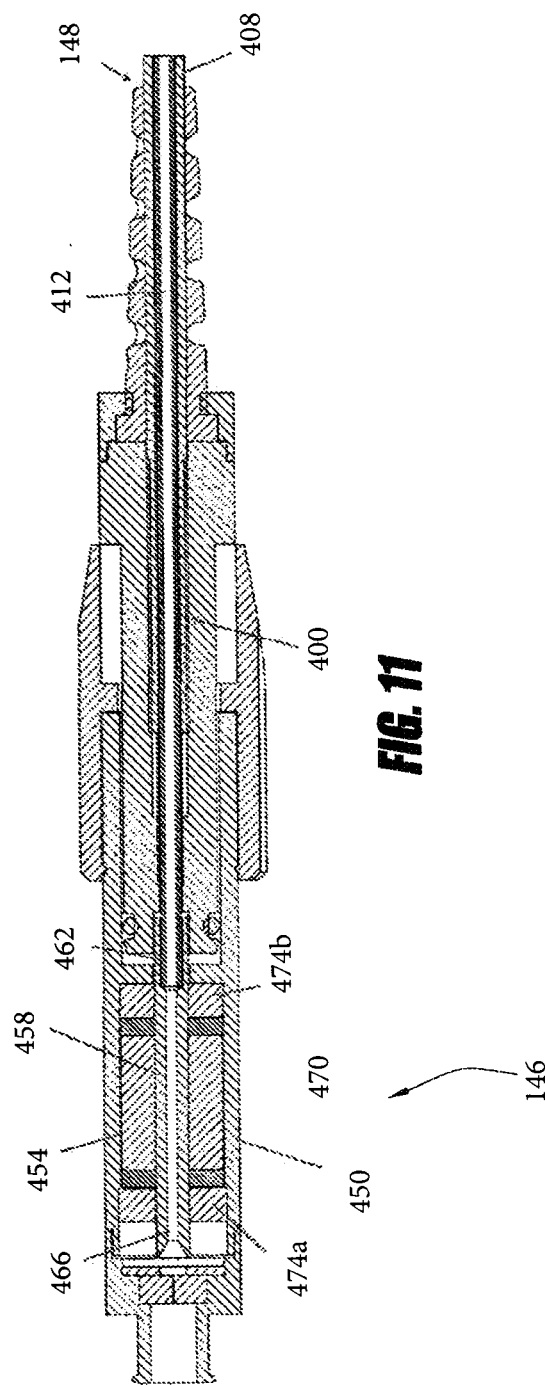
FIG. 11 is a cross-sectional view of a proximal portion of the catheter assembly, taken through the section plane 11-11 on FIG. 1A.

A torque coupling system is provided for transferring torque generated by the drive system to the impeller assembly 116. The torque coupling system is discussed further in Section II(C)—Torque Coupling System (as discussed below), but in general can include magnetic interface between the motor 14 and a drive assembly 146 disposed at the proximal end 104 of the catheter assembly 100. The drive assembly 146 is coupled with a proximal end of an elongate drive shaft 148 in one embodiment. The drive shaft 148 extends between the drive assembly 146 and the impeller assembly 116. A distal portion of the drive shaft 148 is coupled with the impeller assembly 116 as discussed below in connection with one embodiment illustrated in FIGS. 4A and 4B. FIG. 11 shows one manner of coupling the proximal end of the drive shaft 148 with the drive assembly 146.

As discussed above, the heart pump 10 may also include an infusion system 26. FIG. 1A shows that the infusion system 26 can include an infusion inflow assembly 150 provided adjacent to the proximal end 104 in one embodiment. The infusion assembly 150 can be one component of an infusion system that is configured to convey one or more fluids within the catheter assembly 100. The fluids can be conveyed distally within the catheter assembly 100, e.g., within the catheter body 120, to facilitate operation of the impeller assembly 116, some aspect of a treatment, or both. In one embodiment, the infusion system is configured to convey a lubricant, which can be saline, glucose, lactated Ringer's solution, acetated Ringer's solution, Hartmann's solution (e.g., including compound sodium lactate), and D5W dextrose solution. In another embodiment, the infusion system is configured to convey a medication, or a substance that both acts as lubricant and medication. As sometimes used herein "infusant" is intended to be a broad term that includes any fluid or other matter that provides performance enhancement of a component of the heart pump 10 or therapeutic benefit, and can be wholly or partly extracted from the system during or after operation of the pump.

In one embodiment, the infusion inflow assembly 150 includes a catheter body 154 having a luer or other suitable connector 158 disposed at a proximal end thereof and an inflow port in fluid communication with one or more lumens within the catheter assembly 100. A lumen extending through the catheter body 154 is adapted to be fluidly coupled with a fluid source connected to the connector 158 to deliver the fluid into the catheter assembly 100 and through one or more flow paths as discussed below in connection with FIGS. 4A, 4B, and 7-7C.

FIGS. 1A and 12 show that the catheter assembly 100 in various embodiments also includes an outlet positioned at a location that is outside the patient when the heart pump 10 is in use to allow infusant to be removed from the pump and from the patient during or after the treatment. The outlet can be fluidly coupled with an infusant return flow path in the catheter body 120 through a fluid port 144 disposed at the proximal end 104.

The catheter assembly 100 can also include a sheath assembly 162 configured to constrain the impeller assembly 116 in a low profile configuration in a first state and to permit the impeller assembly 116 to expand to the enlarged configuration in a second state. The sheath assembly 162 has a proximal end 166, a distal end 170, and an elongate body 174 extending therebetween. In one embodiment, the elongate body 174 has a lumen extending between the proximal and distal ends 166, 170, the lumen being configured to be slidably disposed over the catheter body 120. The arrangement permits the sheath assembly 162 to be actuated between an advanced position and a retracted position. The retracted position is one example of a second state enabling the impeller assembly 116 to expand to an enlarged configuration. The advanced position is one example of a first state that enables the impeller assembly 116 to be collapsed to the low profile configuration. In some embodiments, a luer 102 or other suitable connector is in fluid communication with the proximal end 166 of the sheath assembly 162. The luer 102 can be configured to deliver fluids to the catheter assembly 100, such as priming fluid, infusant, or any other suitable fluid.

FIG. 1A illustrates a retracted position, in which the distal end 170 of the elongate body 174 is at a position proximal of the impeller assembly 116. In an advanced position, the distal end 170 of the elongate body 174 is positioned distal of at least a portion of the impeller assembly 116. The sheath assembly 162 can be configured such that distal advancement of the distal end 170 over the impeller assembly 116 actuates the impeller assembly 116 from an enlarged state to a more compact state (or low profile configuration), e.g., causing a change from the second state to the first state, as discussed above.

Figure 4A:
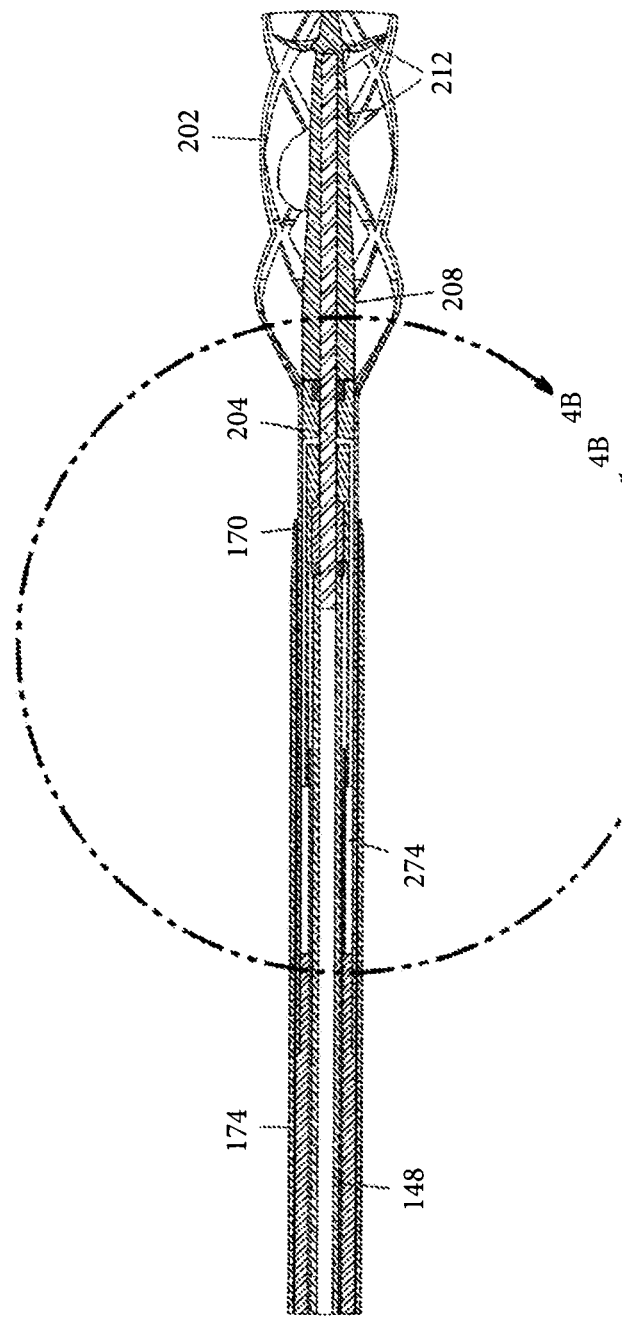
FIG. 4A is a cross-sectional view of a distal portion of the catheter assembly, taken through the section plane 4A-4A shown in FIG. 2.
Figure 4B:
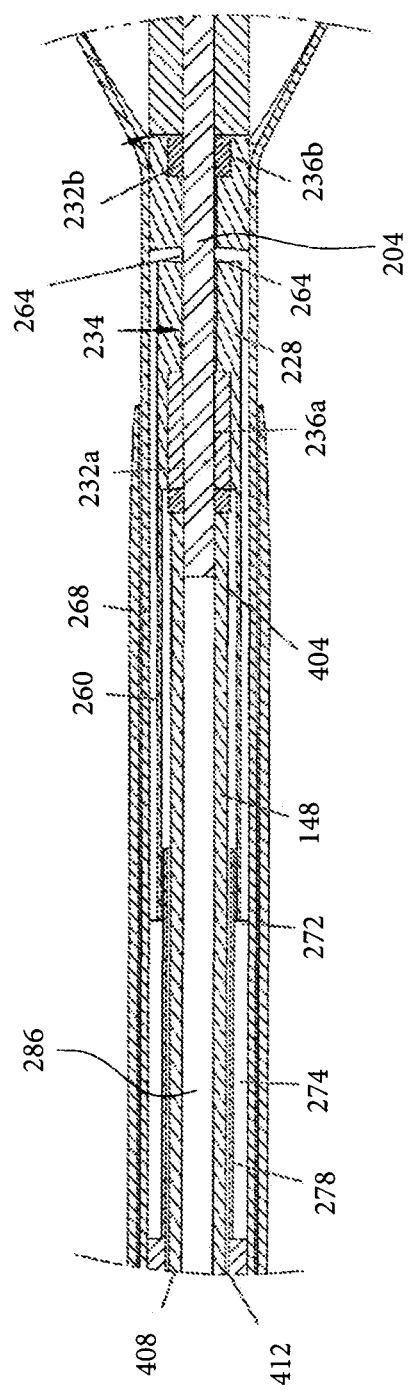
FIG. 4B is a detail view of the distal portion of the catheter assembly, taken at 4B-4B shown in FIG. 4A.

FIGS. 4A & 4B show the elongate body 174 as a single layer structure from the inner surface to the outer surface thereof. In another embodiment, the elongate body 174 has a multilayer construction. In one arrangement, the elongate body 174 has a first layer that is exposed to the catheter body 120 and a second layer exposed that corresponds to an outer surface of the catheter assembly 100. A third layer can be disposed between the first and second layers to reinforce the elongate body 174, particularly adjacent to the distal end thereof to facilitate collapse of the impeller assembly 116. In another construction, a reinforcing structure can be embedded in an otherwise continuous tubular structure forming the elongate body 174. For example, in some embodiments, the elongate body 174 can be reinforced with a metallic coil.

Figure 2:
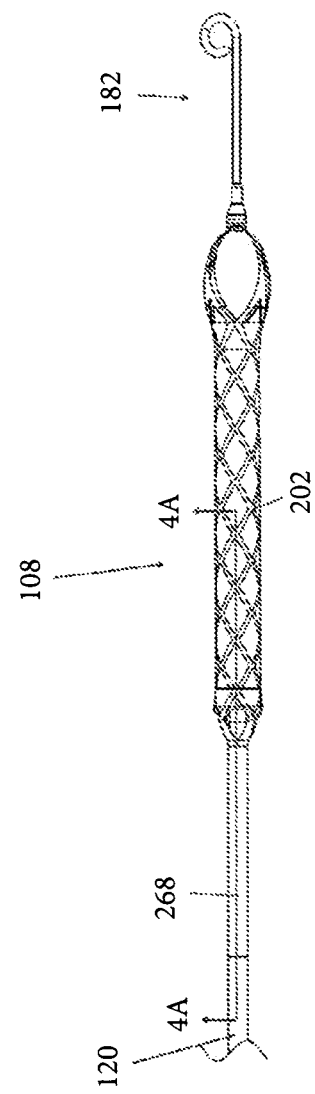
FIG. 2 is a detail view of a distal portion of the catheter assembly illustrated in FIG. 1A.

FIG. 2 show that an impeller housing 202 is disposed at the distal end 108. The impeller housing 202 can be considered part of the impeller assembly 116 in that it houses an impeller and provides clearance between the impeller and the anatomy to prevent any harmful interactions therebetween. The housing 202 and the impeller are also carefully integrated to maintain an appropriate flow regime, e.g., from distal to proximal or from proximal to distal within the housing.

FIGS. 1A and 2 also show that the distal end 108 of the catheter assembly 100 includes an atraumatic tip 182 disposed distal of the impeller assembly 116 in one embodiment. FIG. 1A shows that the atraumatic tip 182 can have an arcuate configuration such that interactions with the vasculature are minimally traumatic. The tip 182 can also be configured as a positioning member. In particular, the tip 182 can be rigid enough to help in positioning the impeller assembly 116 relative to the anatomy. In one embodiment, the tip 182 is rigid enough that when it is urged against a heart structure such as the ventricle wall, a tactile feedback is provided to the clinician indicating that the impeller assembly 182 is properly positioned against the heart structure.

II. Impeller Rotation and Support

The impeller assembly 116 can take any suitable form, but in various embodiments includes an impeller 200 adapted to move a fluid such as blood from an inlet to an outlet of the catheter assembly 100. In certain embodiments the impeller 200 can be cantilevered or otherwise supported for rotation primarily at one end.

Figure 3:
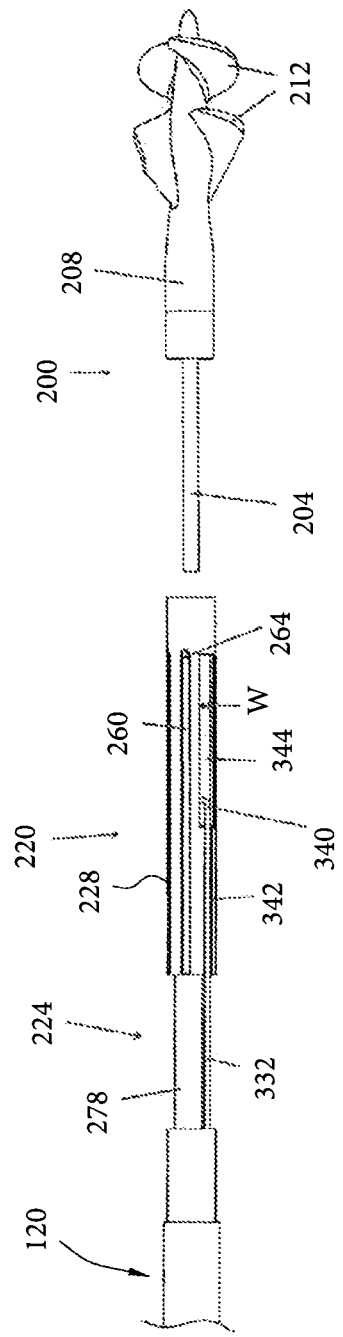
FIG. 3 is an exploded view of a portion of an impeller assembly of the catheter assembly of FIG. 1A.

FIG. 3 shows that the impeller 200 includes a shaft 204, a central body or hub 208, and one or more blades 212.

Figures 1, 9B:
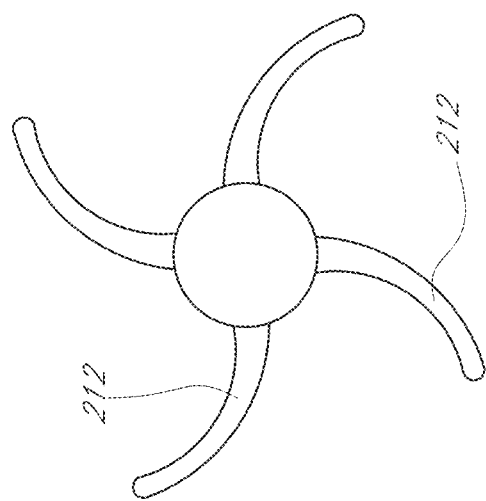
Figures 2, 9B:
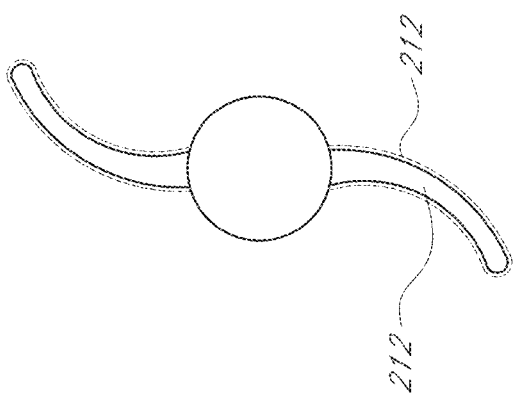
Figure 10:
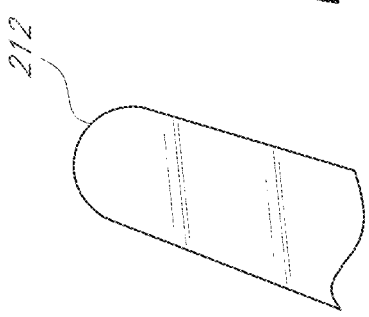
Figure 10A:
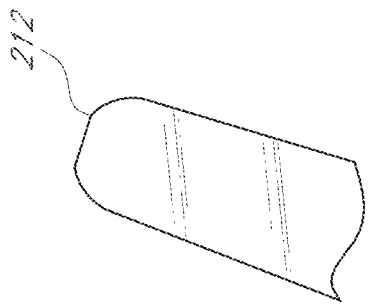

The shaft 204 and hub 208 can be joined in any suitable fashion, such as by embedding a distal portion of the shaft within the hub 208. The blades 212 can be spaced out proximal to distal along the axis of the shaft. In some embodiments, the blades 212 are provided in blade rows. FIG. 9 shows that the distal end of the shaft 204 can extend at least to an axial position corresponding to one of the blade rows. In some embodiments, the shaft 204 can be solid. In other embodiments, the shaft 204 has a lumen extending axially through the hub so that a guidewire can be passed through the catheter assembly 100. Details of variations with a lumen are discussed further in U.S. application Ser. No. 12/829,359, filed Jul. 1, 2010, titled *Blood Pump With Expandable Cannula*, which is hereby incorporated by reference herein in its entirety and for all purposes.

A. Infusant Delivery and Removal System

The operation and duty cycle of the impeller assembly 116 can be lengthened by providing a hydrodynamic bearing for supporting the shaft 204. A hydrodynamic bearing can be supported by a lubricant, such as isotonic saline, which can be delivered in a continuous flow. The lubricant can be delivered through the infusion system to an outside surface of the shaft 204. The infusant may be directed onto the shaft from a radially outward location. In some arrangements, the lubricant flow is controlled such that of a total lubricant volume introduced into the proximal end of the cannula, a first portion of the total volume of the lubricant flows proximally along the shaft 204. In some embodiments, a second portion of the total volume flows distally along the shaft, the first volume being different from the second volume. The second portion of the total volume can be substantially equal to the total volume introduced into the proximal end of the cannula less the first volume.

FIGS. 3 to 8 show various structures for providing rotational support of a proximal portion of the shaft 204 within the distal portion of the catheter assembly 100. For example, as shown in FIG. 3, a bearing assembly 220 can be disposed at a distal end 224 of the multilumen catheter body 120. In one embodiment, the bearing assembly 224 includes a housing 228 (as shown in FIG. 4B) and one or more bearings configured to support the proximal portion of the shaft 204. The bearing assembly 224, as illustrated in more detail in FIG. 4B, includes a plurality of bearings 232a, 232b disposed within the bearing housing 228. Various materials that can be used for the bearings are discussed below.

Figure 6:
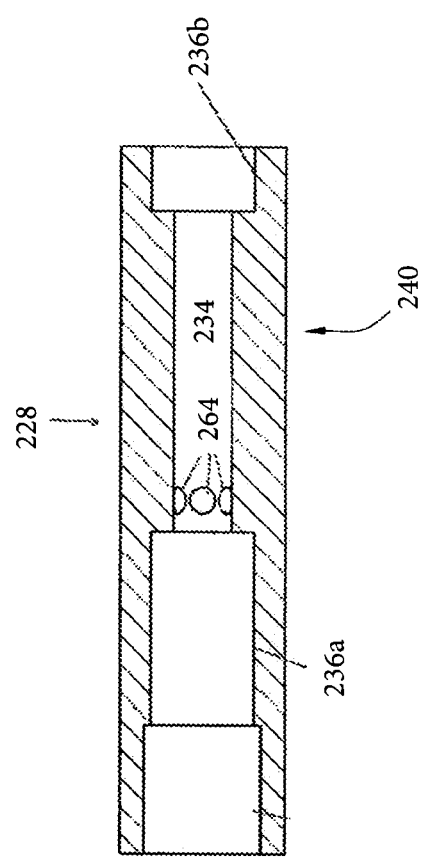
FIG. 6 is a cross-sectional view of a bearing housing of the bearing assembly of FIG. 5.

FIG. 6 shows that the bearing housing 228 has a lumen 234 extending therethrough with a proximal enlarged portion 236a and a distal enlarged portion 236b. The housing 228 comprises a shoulder defining a narrow portion 240 of the lumen 234 disposed between the enlarged portions 236a, 236b. The first and second bearings 232a, 232b can be disposed within the enlarged portions 236a, 236b of the bearing housing 228.

In one arrangement, the proximal end of the shaft 204 (e.g., as shown in FIG. 4A) is received in and extends proximally of the second bearing 232b. In some embodiments there can be one bearing (e.g., only bearing 232a), while in other embodiments both bearings 232a and 232b can be used. In some embodiments, the bearing(s), e.g., bearings 232a and/or 232b, can be friction fit or interference fit onto the impeller shaft 204. Accordingly, the shaft 204 can be supported for rotation by the bearings 232a, 232b as well as in the narrow portion 240 of the housing 228. In embodiments where the bearing(s) 232a, 232b are friction or interference fit onto the shaft, the bearing(s) 232a, 232b can be configured to rotate with the shaft 204 relative to the bearing housing 228. Further, the bearing(s) 232a, 232b can have a relatively large clearance with the bearing housing 228. The clearance between the shaft 204 and the bearing housing 228, at regions that are not coupled with the bearing, can be in the range of about 0.0005 to about 0.001 inch. In certain embodiments, the clearance can be within a larger range, such as at least about 0.0005 inches, about 0.001 inches or up to about 0.005 inches. In embodiments with multiple bearing(s) 232a, 232b, the clearance can be different for the bearings 232a, 232b, such as providing a larger clearance at the proximal bearing 232a.

Figure 5:
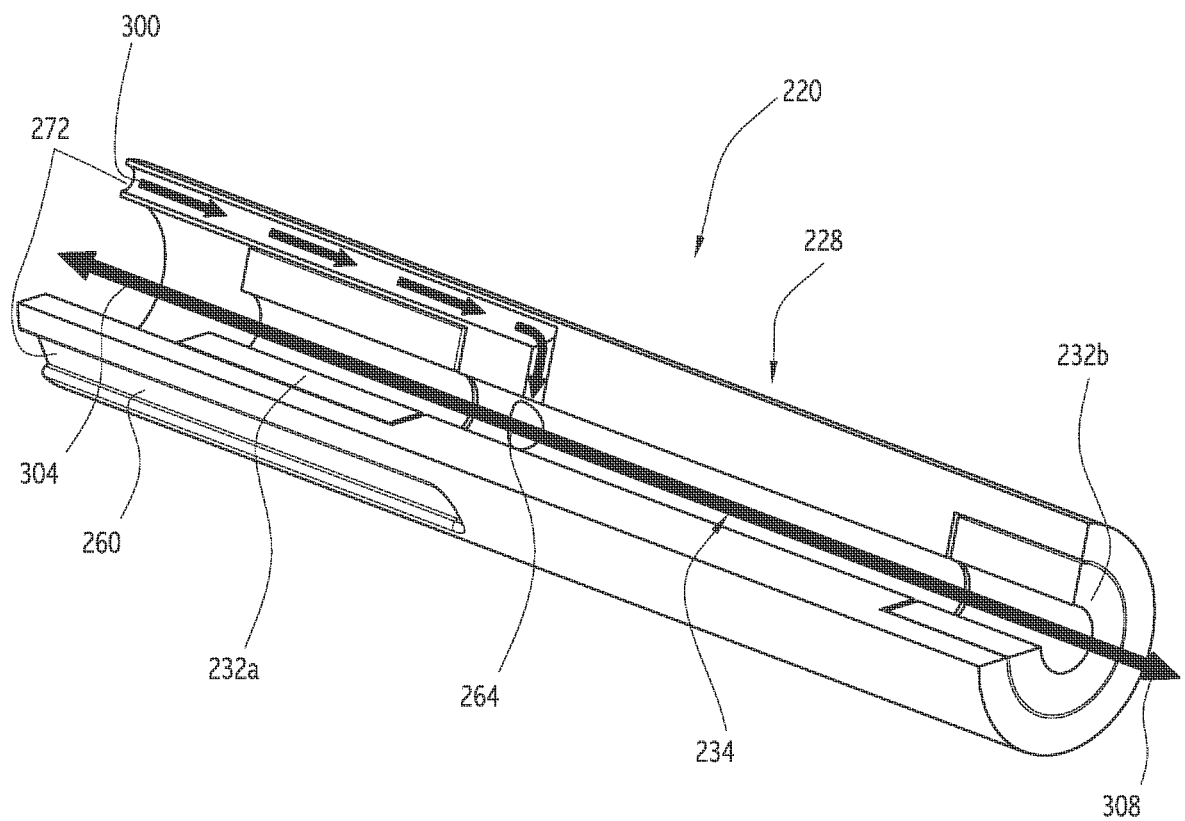
FIG. 5 is a cross-sectional perspective view of a bearing assembly of the catheter assembly of FIG. 1A.

In other embodiments, such as in FIG. 5, the bearing(s) 232a, 232b may not be friction or interference fit onto the shaft 204. In these embodiments, the bearing(s) 232a, 232b may be disposed within the bearing housing 228, for example by an interference or press fit. The shaft 204 may then rotate with respect to the bearing(s) 232a, 232b, and there can be a clearance between the shaft 204 and the bearing(s) 232a, 232b. The clearance between the shaft 204 and the bearings 232a, 232b can be in the range of about 0.0005 to about 0.001 inch. In certain embodiments, the clearance can be within a larger range, such as at least about 0.0005 inches, about 0.001 inches or up to about 0.005 inches. The clearance can be different for the bearings 232a, 232b, such as providing a larger clearance at the proximal bearing 232a. In certain embodiments, the bearing housing 228 may provide a thrust surface for bearing axial loads. In other embodiments, there may be other bearings located either distally or proximally of the bearing housing 228 that are configured to bear axial loads. In other embodiments, the fit between the bearings 232a, 232b and the shaft 204 can be tight, which can also assist in bearing axial loads in some aspects.

At least the proximal portion of the shaft 204 can be made of a material that will not corrode or otherwise be made to be inert when immersed in the lubricant or other infusant. The material may be one that will not corrode in isotonic saline. Suitable materials may include a wide variety of metals, including alloys, and at least saline-resistant stainless steel and nickel-based alloys. Also, the shaft 204 could be made as a composite to include advantageous properties of a plurality of materials. In some cases the shaft 204 could be formed as a polymer. The class of polymers selected would include those that can form a shaft 204 of a certain stiffness suitable in this application. For example, polycarbonate or PEEK could be used. In certain configurations, the polycarbonate, PEEK, or other suitable polymer can provide enhanced performance by being combined with a second material or structure. A glass or carbon filled polycarbonate or other stiff polymer could also be used.

As discussed above, a hydrodynamic bearing between the shaft 204 and the bearings 232a, 232b may be utilized in various embodiments. In one such arrangement, a continuously replenished fluid film is provided at least between the inner wall of the bearing housing and an adjacent moving structure, such as the impeller shaft or an outer surface of a bearing. For example, the bearing housing 228 can be configured to permit a lubricant to be delivered therethrough into the lumen 234. The bearing housing 232 can include a plurality of channels 260 disposed therein extending proximally from a plurality of ports 264 located at the narrow portion 240 of the housing 228. Each port 264 can communicate with one of the channels 260 to provide fluid communication into the lumen 234.

As shown in FIG. 5, the channels 260 can be formed in the wall of the housing 228. In one embodiment, the channels 260 are formed as open depressions, e.g., as flutes, extending along the housing 228. In this embodiment, the channels 260 can be enclosed by a separate structure, such as a separate outer sleeve, that is disposed around the housing 228. FIG. 4B shows that a proximal portion 268 of the impeller housing 202 can be sized to tightly fit over the outer surface of the bearing housing 228, enclosing the radially outward portion of the channels 260. In this arrangement, at least a portion of a flow path is formed between an outer surface of the bearing housing 232 and a separate outer sleeve.

Fluid communication between the port 264 in the bearing housing 228 and the infusion inflow assembly 150 can be by any suitable combination of lumens within the catheter assembly 100. For example, in one embodiment, each of the channels 260 has a proximal port 272 that communications with an annular space 274 formed in the catheter assembly 100. The annular space 274 can be formed between a plurality of separate overlaid structures in the catheter assembly 100. FIGS. 4A and 4B show that the annular space 274 is formed between an outer surface 278 of the multilumen catheter body 120 and an inner surface of the proximal length 268 of the housing 202.

Figure 7C:
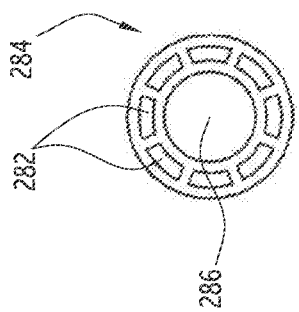
FIGS. 7A-7C show variations of the catheter body of FIG. 7.
Figure 7B:
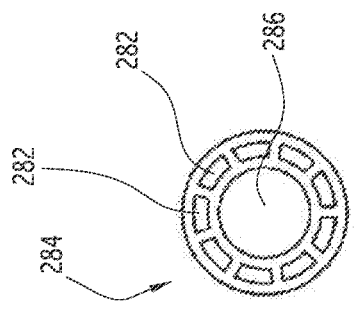
Figure 7A:
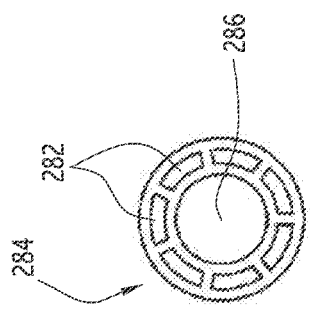

Fluid communication is provided in the catheter assembly 100 between the space 274 and the infusion inflow assembly 150. For example, a plurality of lumens 282 formed in the multi-lumen catheter body 120 can be dispersed circumferentially about the catheter body 120 at a peripheral circumferential region 284, as illustrated in FIGS. 7-7C. The peripheral position of the lumens 282 enables a central area of the catheter body 120 to be dedicated to a central lumen 286. By providing a plurality of smaller lumens 282 located at the periphery, a relatively large flow rate can be delivered through a relatively small circumferential band (when considered in cross-section) of the catheter body 120. Each of the lumen 282 has a distal port 290 that communicates with the space 274.

A proximal portion of the lumens 282 can take any suitable form. For example, the lumens 282 can communicate at their proximal end with a flow diverting structure (not shown) that is in fluid communication with the infusion inflow assembly 150. As described herein, in some embodiments the lumen 282 can be disposed circumferentially about the central lumen 286. The catheter assembly 100 can include a flow diverting structure or connector, e.g., disposed about the proximal end of the catheter body 120 that is configured to divert the infusant into the lumens 282 for distally directed flow therein. In other embodiments, the catheter assembly 120 can include a flow diverting structure disposed adjacent the distal end thereof that is configured to divert the infusant into the lumens 282 from the central lumen 286 for proximally directed flow in the lumens 282.

FIG. 5 includes arrows that illustrate the flow of infusant into the bearing assembly 220. In one arrangement, the inflow of infusant is indicated by an arrow 300 which is shown pointing distally within one of the channels 260 of the bearing housing 228. The infusant flow enters the bearing housing through the ports 264. Although flow is shown in one channel 260, corresponding flow may be provided in each of a plurality of channels 260 disposed around the central lumen 234. An arrow 304 illustrates that at least a portion of the infusant delivered through the port 264 may flow generally proximally within the bearing housing 228. An arrow 308 illustrates that at least a portion of the infusant delivered through the port 264 may flow generally distally within the bearing housing 228.

FIG. 5 illustrates the arrows 304, 308 as proximally and distally directed, respectively. However, the high speed rotation of the impeller shaft 204 within the housing 228 will create a thin film of lubricant spacing the impeller shaft 204 from the surfaces of the bearings 232a, 232b. This thin film will extend all the way around the shaft 204 and thus each portion of the flow will have a spiral or helical flow direction.

The bearings 232a, 232b can have different configurations to enhance the performance of the pump 10. For example, the proximal bearing 232a can be longer along the longitudinal axis of the bearing housing 228 than the distal bearing 232b. A longer proximal bearing 232a is believed to better control runout of the shaft 204. Better runout control on the shaft 204 is believed to enhance the control of the position of the blades 212 relative to the housing 202. Less runout reduces excessive variation in the gap between the blades 212 and the housing 202, providing biocompatibility benefits such as reduced hemolysis.

In some embodiments, such as those in FIG. 5 where the bearings 232a, 232b are not friction fit or interference fit onto the shaft 204, the distal bearing 232b has a smaller inner diameter than the proximal bearing 232a. If the shaft 204 has a constant diameter, the smaller inner diameter should provide greater control of angular deflection of the shaft. Controlling angular deflection can enhance relative position control of the blades 212 and housing 202, providing blood handling benefits such as reduced hemolysis. A smaller clearance could also be provided by enlarging the diameter of the shaft 204 at the axial position of the distal bearing. In some embodiments, the larger inner diameter of the bearing 232b enables a larger volume of lubricant to flow proximally and a lesser volume to flow distally in the lumen 234.

The continuous introduction of lubricant maintains a constant, predictable and durable rotational bearing state between stationary component, e.g., the bearing housing 282, and a moving component, e.g., the shaft 204, a component of the bearings 232a, 232b, or both the shaft 204 and a component of the bearings 232a, 232b. Also, continuous lubricant inflow provides a means for removing heat generated by the relative motion between the shaft 204 and the bearings. Also, the infusant can create fluid pressure within the catheter assembly 100 that can push debris generated within or by the pump 10 out of the bearing housing 220. Enhancing the volume of infusant that flows along the path indicated by the arrow 304 enhances the likelihood that debris generated by or present in the pump will be removed from the proximal end rather than to be trapped inside the distal portion of the catheter assembly 100.

Another technique for controlling infusant flow in the lumen 234 is to locate the port 264 between the bearings 232a, 232b and closer to one of the bearing. For example, the ports 264 can be located adjacent to the proximal bearing 232a in one embodiment. This provides a shorter path of egress out of the narrow portion 240 of the bearing housing 228 in the proximal direction.

Figure 8:
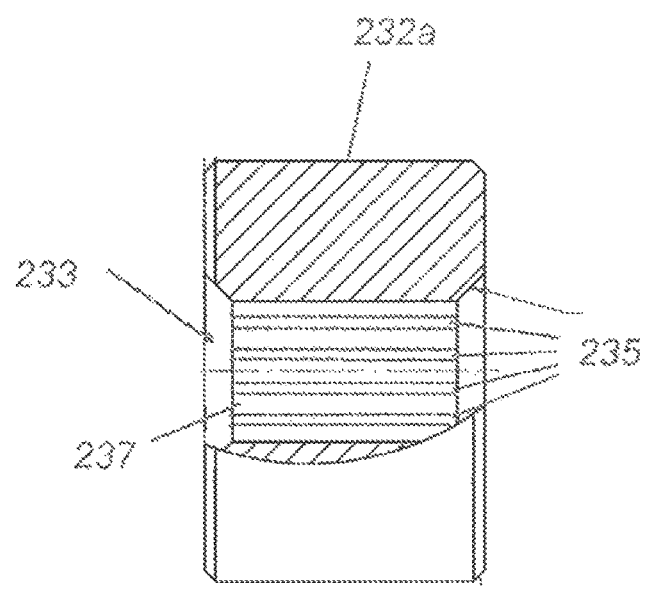
FIG. 8 illustrates a surface configuration of one embodiment of a bearing adapted to enhance or control flow of an infusant in the bearing assembly of FIG. 5.

Other strategies for controlling the flow of infusant within the bearing housing 228 include modifying a surface within one or more of the bearings 232a, 232b. FIG. 8 shows a surface modification 233 provided in a bearing 232a to enhance proximally directed flow. The surface modification 233 comprises a plurality of axially oriented grooves 235 in one embodiment. In another embodiment, the surface modification 233 includes one or more spiral grooves. The spiral grooves can be formed with a groove entrance that is substantially parallel with a flow direction of infusant between the bearings 232a, 232b such that a reduction of velocity of the flow is minimized. In one embodiment, each spiral groove includes at least about 3 turns disposed on the inner surface of the bearing between the proximal and distal ends of the bearing. In another embodiment, each spiral groove has adjacent turns that are spaced apart by a minimum pitch of 0.125 inches (3.2 mm). In another embodiment, each spiral groove has an axial density of about 32 turns per inch (about 1.3 turns per mm). The grooves are formed in the surface 237 of the bearing 232a upon which the impeller shaft 204 is supported. The grooves 235 locally enlarge the clearance between the shaft 204 and the surface 237 so that a greater volume of infusant can flow distal-to-proximal across the bearing 232a. The surface modification 233 reduces back-pressure limiting the distal-to-proximal flow across the bearing 232a.

In other embodiments, it may be desirable to enhance distally directed flow. For example, the infusant may be provided with a fluid intended to be delivered to the patient. In such embodiments, the surface modification 233 can be provided on the distal bearing 232b. In certain embodiments, both proximal and distal bearings 232a, 232b are provided with flow enhancing modifications to enhance heat transfer or purging of the bearing assembly 220. In such embodiments, one of the bearings may have a greater degree of flow enhancement provided on the bearing surface.

The arrangement of the bearing assembly 220 can be a factor in selecting an appropriate infusant. Saline is a preferred infusant, but other sufficiently biocompatible infusants could be used. Other embodiments are configured such that little or no infusant flows out of the pump into the patient. For such embodiments, other infusant fluids can be used, such as glucose.

FIG. 7 illustrates further features of the catheter body 120. The catheter body 120 comprises an inner most portion 320 that defines the central lumen 286. The inner most portion 320 is disposed within, e.g., circumferentially surrounded by, the peripheral circumferential region 284. A continuous outer circumferential region 324 can be provided around the peripheral circumferential region 284 to fully enclose the lumens 282, discussed above. FIGS. 4A and 4B illustrate that a distal end of the inner most portion 320 is configured to be received and secured within a proximal portion of the lumen 234 within the bearing housing 228. FIG. 4B illustrates that a region of overlap can be provided between a distal portion of the inner most portion 320 and a proximal portion of the bearing housing 228. This construction provides a continuous lumen defined in part by the central lumen 286 of the catheter body 120 and in part by the lumen 234 of the bearing housing. In another arrangement, the bearing housing 228 and the catheter body 120 are joined by a coupler that enhances the sealing between infusant inflow through the lumens 282 and the channels 260 and the infusant outflow through the central lumen 286. As discussed further below, this continuous lumen provides a space for the rotation of the shaft 204 of the impeller assembly 116 and the drive shaft 148 of the torque coupling system.

The physical connection between the bearing housing 228 and the catheter body 120 can be achieved in any suitable manner. FIG. 3 illustrates that in one arrangement, a slideable connection is provided. In this arrangement, a rod 332 is provided between the bearing housing 228 and the catheter body 120. The rod 332 can have any suitable configuration, but may have a proximal end configured to be received in a recess or lumen formed in the catheter body 120 and a distal end 340 configured to couple with the bearing housing 228. FIG. 3 shows that the distal end 340 of the rod 332 can be configured to engage with a feature of the bearing housing 228 so that a limited range of sliding is permitted.

In one embodiment, the bearing housing 228 has an elongate channel 342 configured to receive a middle portion of the rod 332 and an enlarged depression 344 located at the distal end of the channel 342. The depression 344 has a width W that is sufficient to receive a wide distal end of the rod 332. The depression 344 can be configured to have an axial length along the housing 228 that can define a range of motion of the bearing housing 228 relative to the catheter body 120.

In one arrangement, the bearing housing 228 is positioned relative to the catheter body 120 and the rod 332 such that the distal portion of the rod 332 is located at the distal end of the depression 344. Thereafter, the catheter assembly 100 can be manipulated such that the bearing housing 228 moves distally relative to the catheter body 120 and the rod 332 such that the distal portion of the rod 332 is located at the proximal end of the depression 344. In the distal position, the impeller assembly 116 is located more distally than in the proximal position. As discussed further below, this enables a variety of techniques for unfurling the impeller blades 212 within the housing 202.

B. Bearing Configurations

Any suitable bearing can be used in the catheter assembly 100. The provision of an infusant for hydrodynamic support enables a wide range of bearing materials to be used. If saline or other more corrosive infusant is used, the bearing must be carefully configured to not degrade within the expected duty cycle of the pump 10. Some polymeric materials are advantageously not degraded by isotonic saline, and are acceptable materials from this perspective. Under the fluid-dynamic conditions, a hydrodynamic bearing that is supported by a biocompatible infusant such as isotonic saline is preferred. It is believed that certain polymer bearings in combination with isotonic saline can support such conditions as 35,000-50,000 psi-ft/min for an appropriate duty cycle. Other aspects that can guide the choice of bearing configurations include minimizing thermal expansion, given the heat that could be generated in the heart pump 10, and minimizing moisture absorption.

Any suitable polymeric material may be used for the bearings 232a, 232b. The polymeric material can include a homopolymer, a copolymer, or a mixture of polymers. The polymeric material can include thermoplastic or thermoset polymers. Examples of polymers that can be used for bearings 232a, 232b include, but are not limited to, one or more of a polyketone, a polyether, a polyacetal, a polyamide-imide, a polyacetal, polyether ether ketone (PEEK), polytetrafluoroethylene (PTFE), and polyphenylene sulfide (PPS).

The polymeric material can also include (e.g., can be mixed, combined, and/or filled with) one or more additives such as a reinforcer and a lubricant. Specific additives include, but are not limited to, graphite, carbon fiber, glass fiber, and PTFE. Those of ordinary skill in the art may appreciate that the additives may be polymeric or non-polymeric. In some embodiments, the polymeric material used for bearings 232a and/or 232b can include PEEK, carbon fiber, PTFE, and graphite. In other embodiments, the polymeric material can include PPS and glass fiber. In yet other embodiments, the polymeric material can include a polyamide-imide polymer, carbon fiber, and graphite. The polymeric material can include any suitable amount of additive(s). For example, the polymeric material can include a total amount of additive(s) in the range of from about 1 wt % to about 50 wt %, based on the total weight of the polymeric material. In other embodiments, the polymeric material used for bearings 232a, 232b may not include any additives.

The polymeric material chosen for bearings 232a, 232b can have particular characteristics that advantageously affect the performance of the bearings. For example, in order to minimize thermal expansion caused by the heat generated in the heart pump 10, a preferred material would be subject to a minimum of dimensional change, and can have a coefficient of thermal expansion in the range of from about $1.2 \times 10^{-5}$ °F.$^{-1}$ to about $25.2 \times 10^{-5}$ °F.$^{-1}$. In other embodiments, the polymer used for bearings 232a, 232b has a coefficient of friction in the range of from about 0.15 to about 0.3. In another example, in order to minimize or prevent water absorption, the selected polymeric material can have a water adsorption in the range of from about 0.01% to about 0.4% over a 24 hour period. In yet another example, the polymeric material can be suitable for high pressure and velocity performance, and can have a limiting pressure-velocity (PV) in the range of from about 20,000 psi-ft/min to about 50,000 psi-ft/min.

The polymeric material used for bearings 232a, 232b may be commercially available. Examples of suitable, commercially-available polymeric materials include, but are not limited to, Ketron PEEK-HPV, Turcite A, Turcite X, Turcite TX, Rulon LR, Rulon J, Rulon 641, Rulon AR, Techtron HPV PPS, Ryton PPS, Torlon 4301, and Torlon 4501. In some embodiments, the polymeric material used for bearings 232a, 232b is Ketron PEEK-HPV.

Of course, other bearing configurations and/or materials would be suitable under other conditions, e.g., with less corrosive infusants or if a hydrostatic or non-hydraulic bearing is used.

C. Torque Coupling Systems

A torque coupling system is provided to rotate the impeller 200 at a high rate to move blood from inside a heart camber to a location within a patient's vasculature in amounts sufficient to sustain the patient or provide treatment to the patient. The torque coupling system couples the impeller 200 with the motor 136, which may be disposed outside the patient. It is expected that the impeller 200 and the drive shaft 148 are to be rotated at 25,000-30,000 revolutions per minute for a period of seven to ten days. To provide reliable performance under these conditions, isotonic saline or other lubricant is provided between the drive shaft 148 and stationary components therearound.

FIGS. 11 and 4B illustrate proximal and distal portions 400, 404 of the drive shaft 148. The proximal portion 400 is coupled with the drive assembly 146 such that rotation of the drive assembly 146 rotates the drive shaft 148. The distal portion 404 of drive shaft 148 is coupled with the impeller shaft 204 such that rotation of the drive shaft 148 causes rotation of the impeller shaft 204. The drive shaft 148 also includes an elongate body 408 that extends between the proximal and distal portions 400, 404. The elongate portion 408 comprises a lumen 412 extending therethrough.

The size of the elongate body 408 may be as small as possible to minimize the cross-sectional profile of the catheter assembly 100. The cross-sectional profile of the catheter assembly 100 corresponds to the crossing profile of the catheter assembly, which limits where the system can be inserted into the vasculature. The lumen 412 is sized to permit a guidewire to be advanced therethrough in some embodiments. The use of a guidewire is optional, but may simplify insertion.

In one embodiment, the elongate body 408 comprises a multi-layer construction. In some embodiments, each layer can include at least one coil wire or a plurality of coil wires all wound in a same orientation. For example, a two-layer, counter-wound wire construction is particularly advantageous. A first layer (e.g., an inner layer) of the elongate body 408 is provided by a coiled wire of nickel-molybdenum-chromium alloy, such as 35NLT or MP35N. In other embodiments, the wire material can be MP35N LT. In one embodiment, the wire has a 0.008 inch diameter and the coil has a 5 filar right-hand wound construction. The outer diameter of the first layer may be about 0.071 inch. A second layer (e.g., an outer layer) of the elongate body 408 can include the same material as the first layer, disposed on the outside of the first layer. The first and second layers can be wound in the same direction, or in opposite directions. For example, in some embodiments the first layer (e.g., an inner layer) can be left-hand wound and the second layer (e.g., an outer layer) can be right-hand wound, or vice versa. In other embodiments, both the first and second layers can be left-hand wound. In yet other embodiments, both the first and second layers can be right-hand wound. The wound coil wire construction can advantageously facilitate proximal and/or distal flow of infusant along the outer layer of the elongate body 408. For example, the outer layer can be constructed such that the infusant travels along the coil and/or in the direction of the winding. Those skilled in the art may appreciate that, depending on the direction of rotation of the elongate body 408, the infusant flow can advantageously be directed either proximally or distally. The second layer may be a 5 filar left-hand wound construction. In one embodiment, each layer is formed using a 0.008 inch diameter wire, in the above-noted coiled configuration. In other embodiments, the elongate body 408 can include three or more coil wire layers, wherein the layers are wound in alternating directions. In some embodiments, the outer diameter of the second layer can be between about 0.072 inch and about 0.074 inch, while in other embodiments the diameter can be much larger or smaller. In some aspects, for example, the outer diameter of the second layer can be about 0.073 inch. The inner diameter of the elongate body 408 can be at least about 0.039 inch in some implementations. In some embodiments, one or more ends of the elongate body 408 can be welded and square cut, for example, with a 0.1 inch maximum weld length on each end. The length of the elongate body 408 can vary, but in some embodiments, the length can be between about 47 inches and 48 inches, for example, about 47.5 inches.

Other materials and other constructions are possible. The elongate body 408 can be made of other non-ferrous metals or other corrosion resistant material or constructions with appropriate modulus. Other materials that could meet the corrosion requirements include stainless steel (e.g., 302, 304, or 316). In certain embodiments, the elongate body 408 can have a structure that enables other materials to be used. For example varying at least one of coil layers, filars, wire diameter, and coil diameter may enable an otherwise less robust material to operate below the fatigue stress of that material.

In another embodiment, a four layer construction is provided. The four layers comprise three wire-wound layers, e.g., similar to the arrangement described above, but included a third wound layer on the outer surface of the second layer. A low friction layer can be disposed on the outside surface of the elongate body 408. One material that could be used as a low-friction layer is PTFE, known commercially as Teflon®. The low-friction layer should be configured to have sufficient wear resistance, such as by selection of the appropriate PTFE material, e.g. polyphenylene sulphone-filled PTFE, and/or by insuring appropriate infusant flow is maintained during the entire duration of use of the device in order to prevent undesirable local elevated temperature of the PTFE material.

The drive shaft 148 operates within the multilumen catheter body 120. Because the drive shaft 148 is rotated at a very high rate when in use within the multilumen catheter body 120, the configuration of the surface forming the central lumen 286 is important. In some embodiments, this inner surface has high lubricity and high wear resistance. One material that can be used for the inner surface of the catheter body 120 is high density polyethylene (HDPE), which provides sufficient lubricity and wear resistance. In one embodiment, the entire multilumen catheter body 120 is formed of HDPE. PTFE provides good lubricity and could be used if made sufficiently wear resistant. One way to increase the wear resistance of PTFE is to impregnate it with polyphenylene sulphone (PPSO$_2$), another is to gamma irradiate the material. One way to increase the lubricity of Polyimide materials is to impregnate it with Graphite, another is to impregnate it with Graphite and PTFE.

FIG. 4B shows a clearance 412 between the elongate body 408 of the drive shaft 148 and the inner surface of the multilumen catheter body 120. The clearance 412 may be about 0.005 inch. Along a diameter between opposite sides of the inner surface of the central lumen 286 and outer surface of the elongate body 408 includes about 0.010 inch of space or diametric clearance. A larger minimum clearance may be desirable if the crossing profile can be enlarged or if other structures of the catheter assembly 100 can be made thinner or eliminated to allow more room between the elongate body 408 and the central lumen 286.

FIGS. 11 and 12 show further details of the drive assembly 146, which is disposed at the proximal end 104 of the catheter assembly 100. The drive assembly 146 includes a drive housing 450 having a recess or cavity 454 disposed therein. The cavity 454 is configured for mounting a rotor support shaft 458 for rotation therein. The support shaft 458 has a proximal end and a distal end and a plurality of components mounted thereon. The distal end of the support shaft 458 has a recess 462 formed therein to receive a proximal end of the drive shaft 148. The support shaft 458 may also have a lumen 466 disposed therein for slideably receiving a guidewire.

A rotor 470 is mounted on an outer surface of the support shaft 458 between sleeve bearings 474a, 474b, as shown in FIG. 12. The rotor 470 can take any suitable form, but in one embodiment includes an elongate magnet 476 disposed between proximal and distal flywheels 478a, 478b.

The proximal end of the support shaft 458 has a tapered port 480 for receiving the guidewire. The proximal end can be configured for engaging the motor 136 in some embodiments. In other embodiments, a magnetic field is induced by the motor 136 in a manner that creates torque and rotation of the shaft 458.

An infusant outflow path 482 is provided within the drive assembly 146. The outflow path 482 is provided between an outer surface of the support shaft 458 and an inner surface 486 of the distal bearing. The flow path 482 continues from the distal bearing 474b radially outwardly along thrust surfaces 490a. The flow path continues proximally between the outer surface of the rotor 470 and the inner surface defining the cavity 454. The flow path 482 continues radially inwardly along the thrust surface 490a toward the support shaft 458. The flow path 482 continues proximally between the support shaft 458 and the proximal bearing 474a. Proximal of the bearing 474a, the flow of infusant exits the catheter assembly 100 through an outflow port 144 through which it can be directed to the waste container 46 or discarded. The flow path is shown in more detail in FIGS. 1, 12, 12A, and 12B.

III. Structures that Facilitate Deployment and Retreival

The catheter assembly 100 can include one or more features that facilitate the deployment and/or retrieval of one or more components of the distal end 108 of the heart catheter assembly 100 (e.g., the impeller assembly 116 or a portion thereof).

A. Optionally-Expandable Diffuser

Figure 13A:
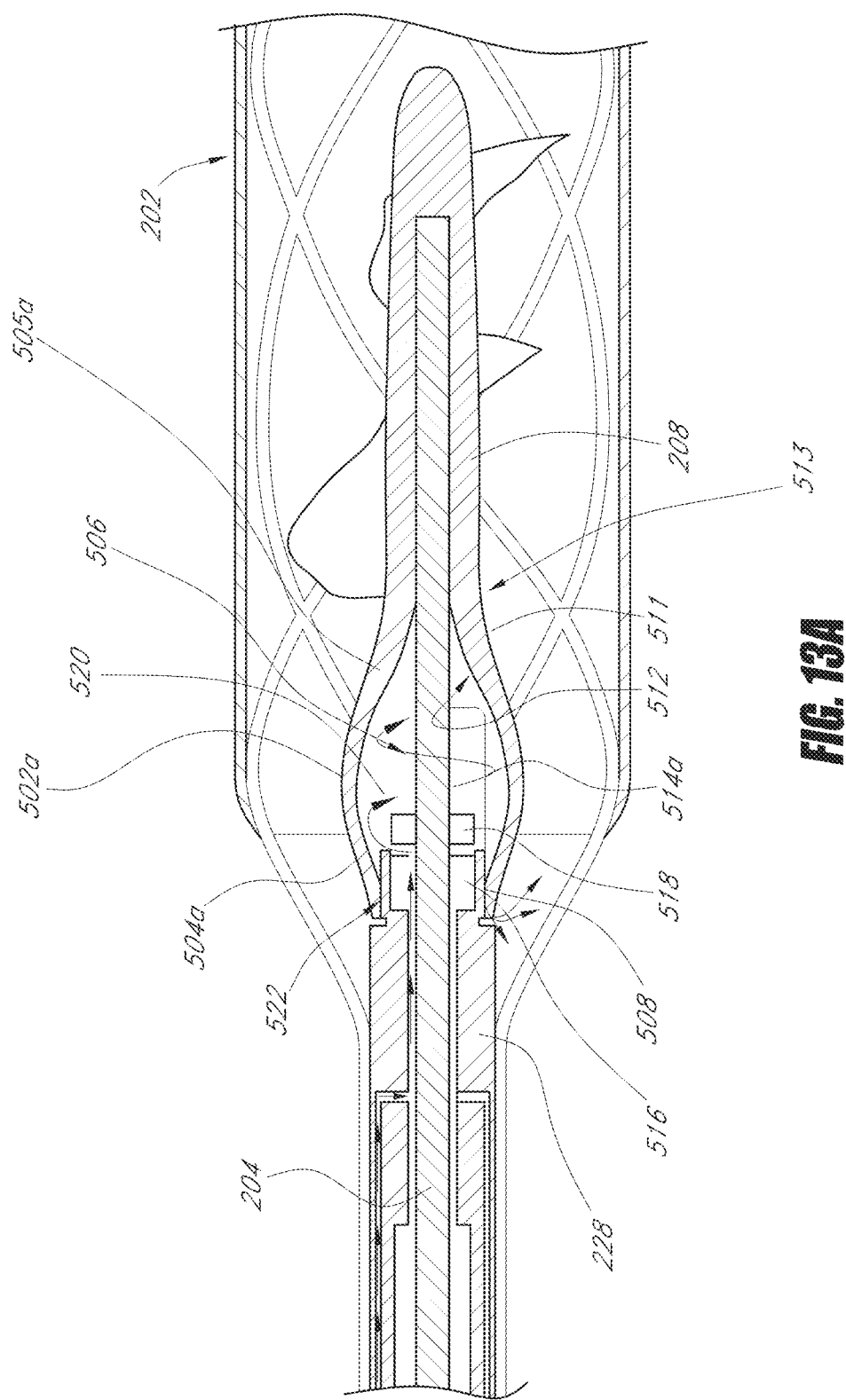
FIGS. 13A-B are cross-sectional views of two embodiments of a blood pump that includes a diffuser.
Figure 13B:
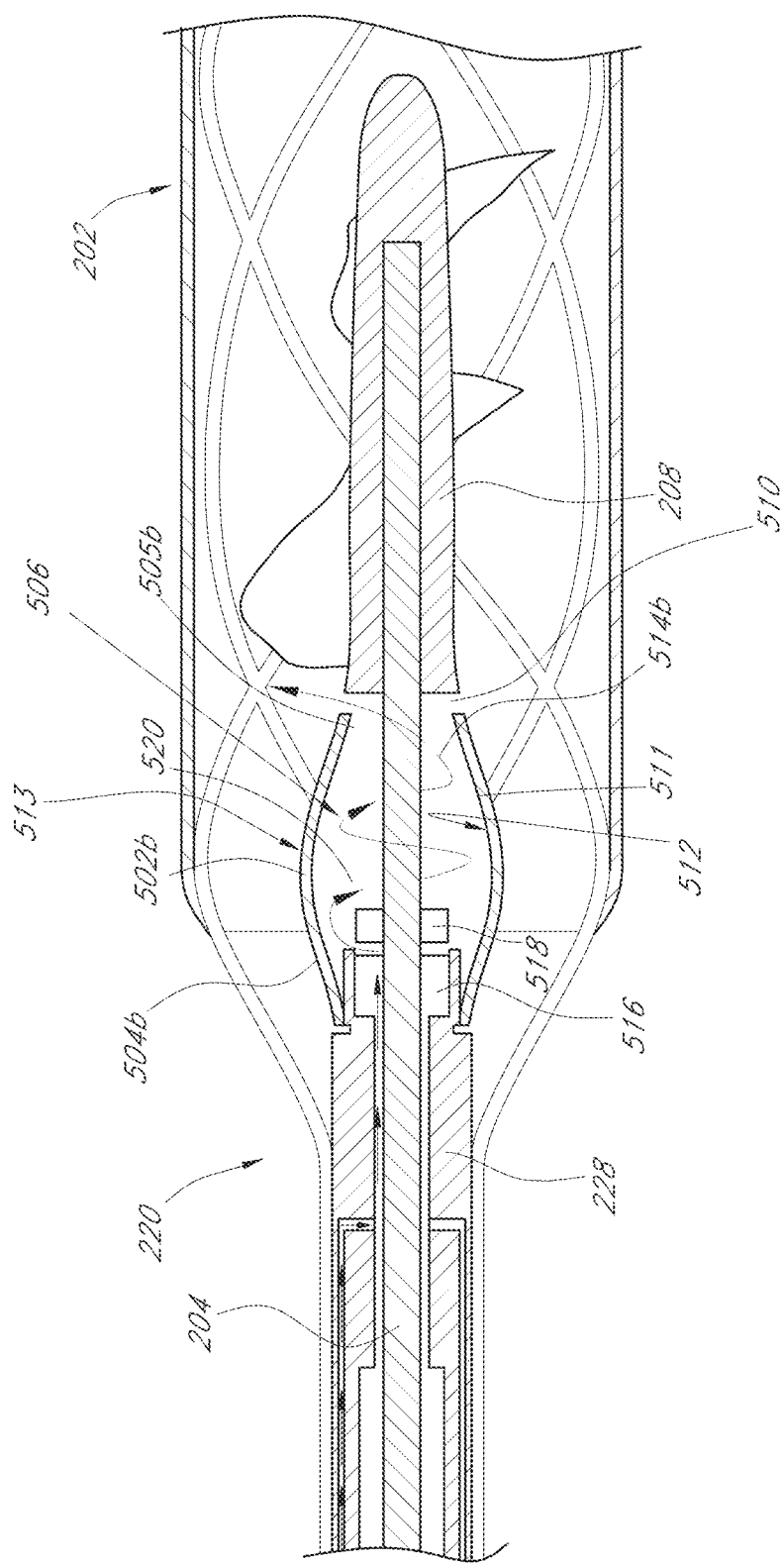

As shown in FIGS. 13A and 13B, the pump can include a diffuser 502a, 502b. As illustrated in FIG. 13A, in some embodiments the diffuser 502a is connected to the impeller hub 208. For example, the diffuser 502a can be integral, or form a unitary structure, with the impeller hub 208. In another example, the proximal end of the impeller hub 208 can include the diffuser 502a. As illustrated in FIG. 13B, in other embodiments, the diffuser 502b is separate from (e.g., not connected to) the impeller hub 208.

The diffuser 502a, 502b can be disposed between the distal end of the elongate body of the catheter body and the impeller. The diffuser 502a, 502b can be configured to be positioned within the housing 202 and adjacent to the proximal opening of the housing. In some embodiments, the diffuser 502a, 502b can be axially aligned with the proximal opening of the housing 202. Advantageously, this configuration can maximize the flow directing capabilities of the diffuser 502a, 502b, as discussed further herein. The diffuser 502a, 502b can be located adjacent the proximal end of the hub 208. The diffuser 502a, 502b can include a proximal end 504a, 504b and a distal end 505a, 505b. The proximal end 504a, 504b of the diffuser 502a, 502b can be positioned adjacent the distal end of the bearing housing 228 (e.g., over a bearing 516 and/or a front thrust washer 518). As shown in FIG. 13A, the proximal end 504a can be separated from the bearing 516 by a gap 522. The gap 522 can have an axial length generally equal to the length of the bearing 516. The gap 522 can also be generally cylindrical with a longitudinal axis that is aligned with the longitudinal axis of the impeller shaft 204. The distal end 505a, 505b can be located adjacent the proximal end of the impeller hub 208. The diffuser 502a, 502b can include a flow directing surface. For example, an outer surface 513 of the diffuser 502a, 502b can form a curved line from the proximal end 504a, 504b to the distal end 505a, 505b, as illustrated in FIGS. 13A-B. As viewed from the proximal or distal end, the diffuser 502a, 502b can have a generally circular cross sectional shape. As shown in FIGS. 13A and 13B, the diameter of the diffuser 502a, 502b can be greatest in the mid section and can taper to a smaller diameter in the distal and/or proximal directions. The diffuser 502a, 502b can have a maximum diameter that is generally greater than the diameter of the hub 208 and/or the bearing housing 228. The diameter of the proximal end 504a, 504b can be generally equal to the diameter of the bearing housing 228. The diameter of the distal end 505a, 505b can be generally equal to the diameter of the hub 208. The diffuser 502a, 502b may be referred to herein as a bulge, and in various embodiments can have a radially enlarged portion disposed downstream of the impeller.

Advantageously, the relatively large diameter and/or the curved outer surface can assist in directing (e.g., diffusing) fluid flow out of the housing 202. The geometry of the diffuser 502a, 502b (e.g., the radius of curvature of the outer surface) can be optimized to control desired fluid properties such as boundary layer flow, laminar flow, and pressure gradients and to reduce outlet flow losses.

The diffuser 502a, 502b can include a wall 511. The wall 511 can include an inner surface 512 and the outer surface 513, described above. The wall 511 can have a thickness extending from the inner surface 512 to the outer surface 513. In some embodiments, the wall 511 can have a generally uniform thickness along the axial length of the diffuser 502a, 502b. One advantage of a generally uniform wall thickness is that the diffuser 502b can be more easily expanded and/or collapsed, as described herein. In other embodiments, the wall 511 can have a variable thickness along the axial length of the diffuser 502a, 502b. For example, as illustrated in FIG. 13A, the thickness of the wall 511 can increase in the distal direction. One advantage of a variable thickness wall is that it can have variable structural strength. For example, a wall having a thickness that increases distally can advantageously have greater strength in areas that are most exposed to oncoming blood flow.

The inner surface 512 can define a chamber 506 through which the impeller shaft 204 can pass. As shown in FIG. 13A, the diffuser 502a can form part of the proximal end of the hub 208 of the impeller 200 (e.g., the hub 208 can be connected to the diffuser 502a). Thus, the diffuser 502a can rotate with the rotating hub 208. The diffuser 502a can also include a proximal cavity outlet 508. As shown in FIG. 13B, the diffuser 502b can be a component separate from the impeller 200. In this embodiment, the diffuser 502b can be stationary when the hub 208 is rotating. The diffuser 502b can also include a distal cavity outlet 510.

There can be many advantages to including a diffuser 502a that is connected to the impeller hub 208. For example, the unitary construction can be easier to manufacture and/or assemble. As described herein, the distal end of the diffuser 502a can be relatively thick and strong (e.g., stiff). In addition, it can be advantageous for the infusant to exit the catheter assembly 100 at the proximal outlet 508, which is generally at the downstream end of the diffuser 502a.

There can also be advantages to including a diffuser 502b that is a structure separate from and not directly attached to the impeller hub 208. In some embodiments, the diffuser 502b can be made from a material that is different from the material used to make impeller hub 208. For example, the diffuser 502b can be made from a material that is relatively more flexible (softer) than the material of the impeller hub 208. In other embodiments, the wall 511 of diffuser 502b can have a generally uniform thickness. These features of diffuser 502b can facilitate the expansion and/or contraction of the diffuser 502b, described further herein.

As shown in FIGS. 13A and 13B, the diffuser 502a, 502b can be generally hollow, as defined by the chamber 506. The diffuser 502a, 502b can be sufficiently hollow and can be made of a relatively flexible material (e.g., a polymer or elastomer) to be expandable and/or collapsible. For example, the maximum diameter of the diffuser 502a, 502b can expand from a first diameter to a second diameter. Advantageously, the collapsible diffuser 502a, 502b can have a deployed, expanded configuration, and a retracted, collapsed configuration. In the deployed, expanded configuration, the diffuser 502a, 502b can have a maximum diameter (e.g., as measured at the mid-section or bulge) that is generally greater than the diameter of the hub 208 and/or the bearing housing 228. In the retracted, collapsed configuration, the diffuser 502a, 502b can have a reduced diameter. For example, in the retracted, collapsed configuration, the diffuser 502a, 502b can have a maximum diameter that is generally less than or equal to the diameter of the hub 208 and/or the bearing housing 228. Although described as having a diameter, those skilled in the art may appreciate that while retracted and/or collapsed, the diffuser 502a, 502b may not have a generally circular cross section. A collapsible diffuser can be advantageous compared to a non-collapsible diffuser because a collapsible diffuser can allow the overall structure to maintain and low profile for the purpose of retracting back into a sheath and for insertion into and/or removal from a patient.

In some embodiments, the relatively flexible material itself may not be significantly expandable (e.g., stretchable and/or elastic). Rather, the terms "expandable" and "collapsible" can refer to the overall expansion and/or collapse of the chamber 506 of the diffuser 502a, 502b. In other embodiments, the relatively flexible material itself may be significantly expandable (e.g., balloon-like).

The chamber 506 can be configured (e.g., sized) to allow fluid (e.g., infusant) flow through the diffuser 502a, 502b. The diffuser 502a, 502b can be configured for fluid communication with a fluid, such as an infusant, that passes through the bearing assembly 220. The bearing assembly 220 illustrated in FIGS. 13A and 13B can have many, if not all, of the same features as described with respect to the bearing assembly 220 illustrated in FIG. 5. As shown in FIGS. 13A and 13B, the infusant can follow an infusant path 514*a*, 514*b* out of the bearing assembly 220 and into the diffuser 502*a*, 502*b* via a passage or cavity 520 between the bearing 516 and the washer 518. For at least a portion of the infusant path 514*a*, 514*b*, the infusant can travel distally. In some embodiments, at least a portion of the infusant path 514*a*, 514*b* can be non-helical (e.g., generally linear). In other embodiments, at least a portion of the infusant path 514*a*, 514*b* can be generally helical. The helical shape of the infusant path 514*a*, 514*b* can be caused at least in part by rotation of one or more components of the impeller assembly 116 (e.g., the impeller shaft 204 and/or impeller hub 208).

As illustrated in FIG. 13A, the infusant path 514*a* can extend from the proximal end 504*a* to the distal end 505*a* and can return back to the proximal end 504*a* to exit the proximal outlet 508 via the gap 522. The portion of the infusant path 514*a* that extends from the proximal end 504*a* to the distal end 505*a* is helical (e.g., can encircle the impeller shaft 204 one or more times along the axial length of the path). The return portion of the infusant path 514*a* can be non-helical (e.g., generally linear). The return portion of the infusant path 514*a* can be non-helical at least in part because the return portion can follow the curved interior surface 512 of the diffuser wall 511. In use, the infusant can exit the bearing assembly 220 at the cavity 520 to enter the chamber 506. At least a portion of the infusant can then follow infusant path 514*a* to travel helically around the impeller shaft 204 in the distal direction until the distal end 505*a* is reached. The infusant then changes direction and turn around to flow proximally along the non-helical return portion of the infusant path 514*a* and through the gap 522 to exit the pump via the proximal cavity outlet 508. Although shown as a single distal-to-proximal line, in some embodiments, exit flow can be induced along and generally following the shape of the inner surface 512 to the proximal cavity outlet 508. In use, as the infusant passes through the gap 522, the infusant can act as a hydrodynamic bearing (e.g., in addition to the hydrodynamic bearing that may be present between the impeller shaft and the bearing housing as described herein). This hydrodynamic bearing can generally be in the shape of a cylinder that extends axially, as defined by the gap 522. Advantageously, this hydrodynamic bearing can reduce friction between the diffuser 502*a* and the bearing housing 228.

As illustrated in FIG. 13B, the infusant path 514*b* can extend from the proximal end 504*b* to the distal end 505*b*. As illustrated in FIG. 13B, the infusant path 514*b* is helical (e.g., can encircle the impeller shaft 204 one or more times along the axial length of the path). In use, as shown in FIG. 13B, generally all of the infusant flows proximally to distally within a distal portion of the bearing assembly 220 and exits the bearing assembly at the cavity 520 to enter the chamber 506. In various embodiments, a portion of the infusant flows proximally within a proximal portion of the bearing assembly 220 through a space between the drive shaft 148 and the catheter body 120. This return flow is discussed above, e.g., in connection with arrow 304 in FIG. 8. At least a portion of the infusant then follows the infusant path 514*b* to travel helically around the impeller shaft 204 in the distal direction and out through the distal cavity outlet 510. As illustrated in FIG. 13B, the distal cavity outlet 510 defines a gap between the distal end 505*b* of diffuser 502*b* and the proximal end of impeller hub 208. In use, as the infusant passes through the distal cavity outlet 510, the infusant can act as a hydrodynamic bearing. This hydrodynamic bearing can generally be in the shape of a cylinder having a length extending axially along the length of the gap and a radius corresponding to the cross sectional radius of the gap. Advantageously, this layer of infusant between the diffuser and the impeller hub can reduce friction between the diffuser 502*b* and the impeller hub 208 when the pump is in operation.

As described herein, the diffuser 502*a*, 502*b* can be expandable. In some embodiments, one or more forces exerted by the infusant can be used to expand the diffuser 502*a*, 502*b*. The flow rate of the infusant can be sufficient to establish an area of positive pressure within the diffuser 502*a*, 502*b*, thereby allowing at least a portion of the infusant to exit adjacent to a distal end of the device. In some embodiments, the static pressure of the infusant entering the chamber 506 can cause the diffuser 502*a*, 502*b* to expand. In any of these embodiments, an inflated diffuser 502*a*, 502*b* can be deflated by interrupting and/or discontinuing the flow of infusant into the diffuser 502*a*, 502*b* and by allowing the infusant to exit the diffuser via the proximal outlet 508 or the distal outlet 510. In some embodiments, the wall is elastic but the pliability is relatively low such that upon removal of the infusant flow a transition from expanded to low profile is rapid. The diffuser 502*a*, 502*b* self-collapses displacing the infusant out of the chamber 506 through one or more small apertures. In addition to promoting quick deflation, the relatively low pliability will provide a uniform diffuser profile, e.g., will not be deformed or deflected by any varying pressure or flow rate of the blood from the impeller 200. A lower infusant pressure configuration can also be provided by increasing the pliability of the structure forming the diffuser 502*a*, 502*b*. The structure can be of enhanced pliability by material selection or constructions (e.g., by being thinner or adopting other balloon-like features).

In other embodiments, the centrifugal force exerted by the infusant as it travels along the helical path 514*a*, 514*b* can be used to expand the diffuser 502*a*, 502*b*. As illustrated in FIG. 13A, the diffuser 502*a* can be connected to the impeller assembly 116. In these embodiments, the diffuser 502*a* and the impeller assembly 116 can be rotated. In use, when the impeller assembly 116 and the diffuser 502*a* are rotated, the infusant can also rotate due to, e.g., shear forces generated from the fluid contact with the rotating diffuser 502*a* and/or the rotating impeller shaft 204. The rotating infusant can exert a pressure on the inner surface 512 to thereby expand the diffuser 502*a* from the collapsed configuration to the expanded configuration. Thus, in some embodiments, the diffuser 502*a* can be centrifugally expanded. In yet other embodiments, the diffuser 502*a* can be expanded using a combination of static and centrifugal forces.

As illustrated in FIG. 13B, the diffuser 502*b* may not be rotatable. In these embodiments, when the impeller shaft 204 is rotated, the infusant can also rotate due to, e.g., shear forces generated from the fluid contact with the rotating impeller shaft 204. As described herein, the rotating infusant can exert a pressure on the inner surface 512 to thereby expand the diffuser 502*b* from the collapsed configuration to the expanded configuration. Thus, in some embodiments, the diffuser 502*b* can be centrifugally expanded. In yet other embodiments, the diffuser 502*b* can be expanded using a combination of static and centrifugal forces.

Infusant exiting the diffuser 502*a*, 502*b* can be continuously replenished with additional infusant via the flow path 514. If the impeller shaft 204 stops rotating, the pressure generated from rotation can decrease to match the pressure acting on the outside of the diffuser 502a, 502b, thereby allowing the diffuser 502a, 502b to collapse.

In yet other embodiments, the diffuser 502a, 502b can be expanded and/or inflated by a combination of static and centrifugal forces. For example, the diffuser 502a, 502b can be expanded and/or inflated by a combination of the static force of the infusant as it enters the chamber 506 and the centrifugal force of the infusant as it travels along the helical path 514.

B. Relatively Axially-Moveable Impeller Housing

As illustrated in FIG. 14B, when the impeller and the diffuser 502 are in the proximal position, at least a portion of the impeller (e.g., the blades 212 and/or the hub) and/or the diffuser 502 may be relatively positioned in a portion of the housing 202 having minimal or no coating, such as an outlet 802 of the housing 202 (e.g., the outlet through which blood is pumped). In some embodiments, the housing 202 can be moved axially relative to the impeller and/or the diffuser 502. In some embodiments, the housing 202 is moved axially over the impeller and the impeller is stationary. Those skilled in the art may appreciate that in some embodiments, the housing 202 may not be configured to move axially relative to the impeller and/or the diffuser 502 (e.g., housing 202 is fixed or stationary relative to impeller and/or the diffuser 502). For example, the housing 202 and the diffuser 502 can be spaced apart by a relatively constant axial distance in all operational states, or at least in a collapsed and an expanded state.

As illustrated in FIGS. 14A and 14B and as described herein, the rod 332 provided between the catheter body 120 and the bearing housing 228 enables a slideable engagement between the catheter body 120 and the bearing housing 228. The distal end of the catheter body 120 can be connected to the proximal portion 268 of the impeller housing 202. The catheter body 120 can translate distally from a proximal position to a distal position, and vice versa, by the application of an axial force described further herein. As described herein, for example with respect to FIGS. 4A-4B, the catheter body 120 can be coupled to the proximal portion 268 of the impeller housing 202. For example, the proximal portion 268 of the impeller housing 202 can be fitted over the distal end of the catheter body 120.

In the proximal position, illustrated in FIG. 14A, the axial position of the outlet 802 can be proximal of the axial position of the proximal-most blade 212. In the distal position, illustrated in FIG. 14B, the axial position of the outlet 802 can generally correspond to the axial position of the proximal-most blade 212. Advantageously, the rod 332 and the enlarged depression 344 can control the axial distance over which the impeller housing 202 is capable of sliding. The rod 332 can also advantageously prevent the bearing housing 228 from rotating with the impeller shaft 204.

Those skilled in the art may appreciate that the axial movement of the catheter body 120 and the impeller housing 202 relative to the impeller and/or the diffuser 502 can have the same relative effect as axially moving the impeller and/or the diffuser 502 relative to the catheter body 120 or the impeller housing 202, even if the impeller and/or the diffuser are not actually moved axially. Accordingly, in some embodiments the catheter body 120 in the proximal position can be referred to as the deployed position of the impeller and/or the diffuser 502. The catheter body 120 in the distal position can be referred to as the retracted position of the impeller and/or the diffuser 502.

The ability of the impeller and/or the diffuser 502 to be retracted and deployed relative to the impeller housing can have many advantages. For example, axial movement of the impeller housing relative to the impeller and/or the diffuser can reduce the profile of the pump to ease insertion and retrieval. In some embodiments, in the retracted position, the impeller hub 208, blades 212, and/or diffuser 502 can be positioned at the same axial location as a portion of the housing 202 that does not have a covering (e.g., the outlet 802). Accordingly, the cross-sectional area of the catheter assembly 100 measured at the axial position of the diffuser 502 in the retracted position, for example, is comparatively smaller than when it is in the deployed position. The smaller cross sectional area can be advantageous for minimizing trauma to a user during insertion into and/or retrieval from the body.

In other embodiments, the retracted position of the impeller and/or the diffuser can be distal of the deployed position of the impeller and/or the diffuser. In some embodiments, the impeller housing can have a rigidity that varies axially. For example, the impeller housing can have a proximal portion that is more rigid (e.g., less flexible) than a distal portion. In these embodiments, the impeller and/or the diffuser can reside in the proximal, rigid portion while in the deployed position. The impeller and/or the diffuser can reside in the distal, flexible portion while in the retracted position. Advantageously, when the impeller and/or the diffuser reside in the flexible portion of the impeller housing, this portion of the pump may be collapsed to a lower profile than would otherwise be achievable if the impeller and/or the diffuser remained in the rigid portion of the impeller housing.

As described herein, the catheter body can be coupled to the impeller housing. The retraction and deployment (e.g., movement between proximal and distal positions) of the impeller housing can be controlled by manipulation of a proximal end of the catheter assembly that results in an application of axial force to the catheter body. For example, the impeller housing can be moved axially by the rotational force applied by a nut disposed at the proximal end of the catheter assembly. A section of the proximal end of the catheter assembly is illustrated in FIGS. 15A and 15B.

Figure 15C:
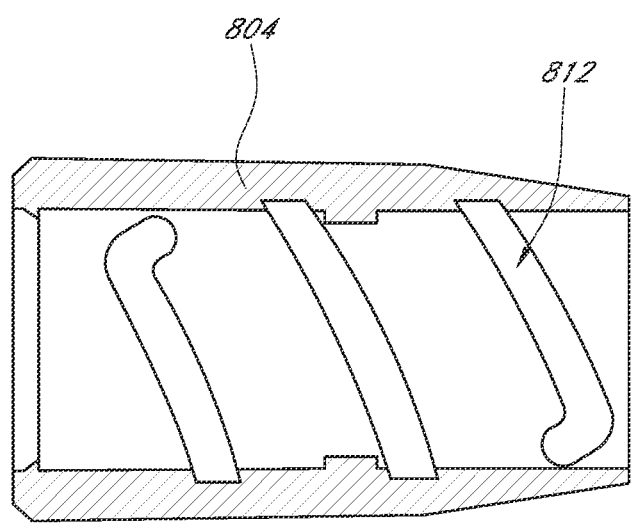
FIG. 15C is a cross-sectional view of a structure for actuating the deployment device illustrated in FIGS. 15A-B.

In some embodiments, axial force is applied to the catheter body via an impeller deployment assembly 800. The impeller deployment assembly includes a nut 804 that is engaged with a portion of the catheter assembly, such as a flow diverter 806. As described herein, the flow diverter 806 can be a part of the infusion inflow assembly 150, illustrated in FIG. 1. The distal end of the flow diverter 806 can be connected to a proximal portion of the catheter body. In some embodiments, the nut 804 can be engaged with a pin 808. The pin 808 can penetrate through the wall of the drive housing 450 and can be coupled with or fixedly attached to the flow diverter 806. The nut 804 can be disposed over at least a portion of the drive housing 450 and/or the flow diverter 806. The nut 804 can include an internal engagement structure that is configured to engage the flow diverter 806 (e.g., via the pin 808). In some embodiments, the internal engagement structure can include internal threading. In other embodiments, the internal engagement structure can include a cam track 812 having first and second ends (e.g., a proximal end and a distal end), as illustrated in FIG. 15C. In these embodiments, the pin 808 can be configured to travel along the cam track 812. The internal engagement structure can be generally helical. The drive housing 450 can also include a longitudinal channel 810 along which the pin 808 can travel.

As illustrated in FIGS. 15A and 15B, the drive housing 450 can contain the support shaft 458 and the drive shaft 148. The drive housing 450 can also capture the nut 804. For example, a retention structure can be formed in the outside surface of the housing 450 to prevent the nut 804 from slipping proximally or distally relative to the housing 450. One embodiment of a retention structure is illustrated below in connection with the deployment device of FIGS. 15D-F but can be included with the deployment device 800 as well. The pin 808 can penetrate the wall of the drive housing 450 and permit axial translation of the flow diverter 806 by acting as a cam. In some embodiments, the support shaft 458 and the thread advance nut 804 may be rotatable but not translatable relative to the drive housing 450.

In use, a rotational force can be applied to the nut 804. This application of rotational force can be converted into an axial force that is applied to the flow diverter 806 and the catheter body. As described herein, the pin 808 can be fixedly attached to the flow diverter 806 at one end and have a second end disposed within the inner surface of the nut 804 along the cam track thereof. The rotation of the nut 804 in a first direction (e.g., clockwise or counter-clockwise) can cause the pin 808 to translate from a proximal position (e.g., proximal end) to a distal position (e.g., distal end) in the longitudinal channel 810. Accordingly, the flow diverter 806, the catheter body, and the impeller housing can also translate from a proximal position to a distal position. As described herein, the distal translation of the catheter body and the impeller housing can improve the ease of the retraction of the impeller hub and the blades into the impeller housing. In embodiments where the outlet 802 is generally free of a polymeric coating, relative movement of at least a portion of the impeller and/or the diffuser proximally into the outlet 802 or distally into a more flexible region of the impeller housing (i.e., mid section of the housing where there is less strut material) can advantageously reduce the profile of the pump upon collapsing into the sheath. In addition, axial adjustment of the impeller housing relative to the impeller can advantageously promote more efficient flow dynamics. In some embodiments, the impeller is positioned closer to the outlet 802 than the middle portion of the housing in order to improve flow dynamics.

A rotational force applied to the nut 804 in a second direction (e.g., counter-clockwise or clockwise) can cause the pin 808 to translate from the distal position to the proximal position. Accordingly, the flow diverter 806, the catheter body 120, and the impeller housing 202 can also translate from a distal position to a proximal position. As described herein, the proximal translation of the catheter body 120 and the impeller housing 202 can effectively result in the deployment of the impeller hub 208 and the blades 212.

Figure 15D:
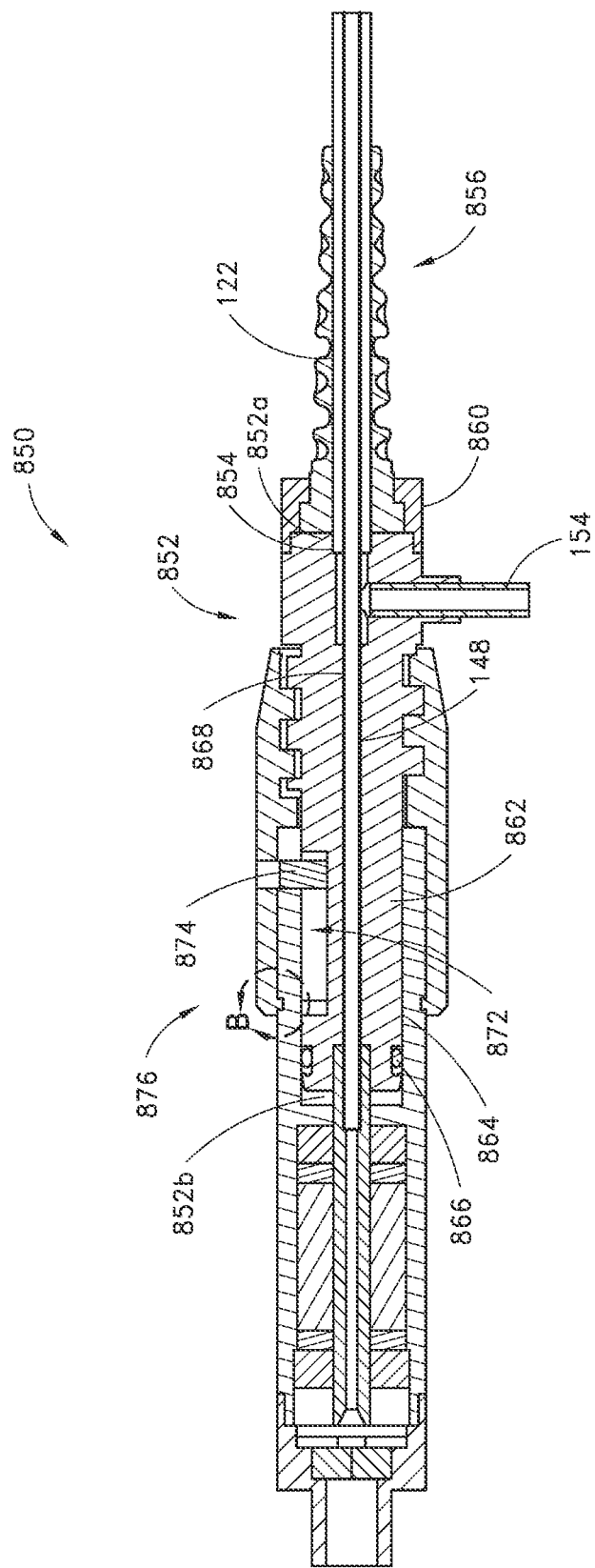
FIGS. 15D-F illustrate further embodiments of deployment devices that can actuate the catheter assembly between deployed and retracted configurations.
Figure 15D:
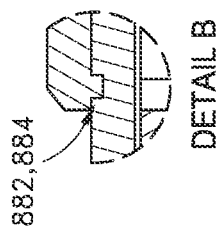
Figure 15E:
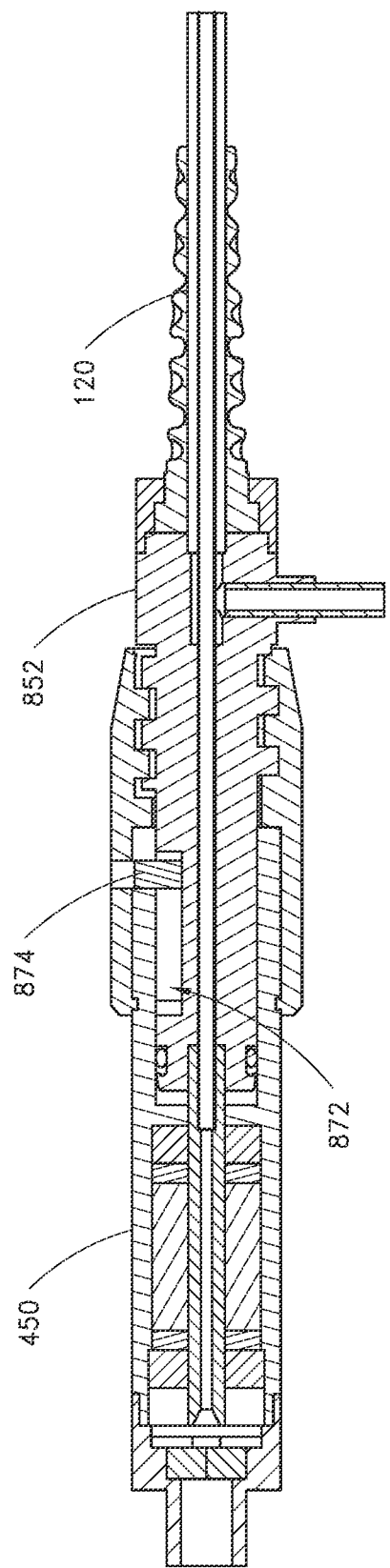
Figure 15F:
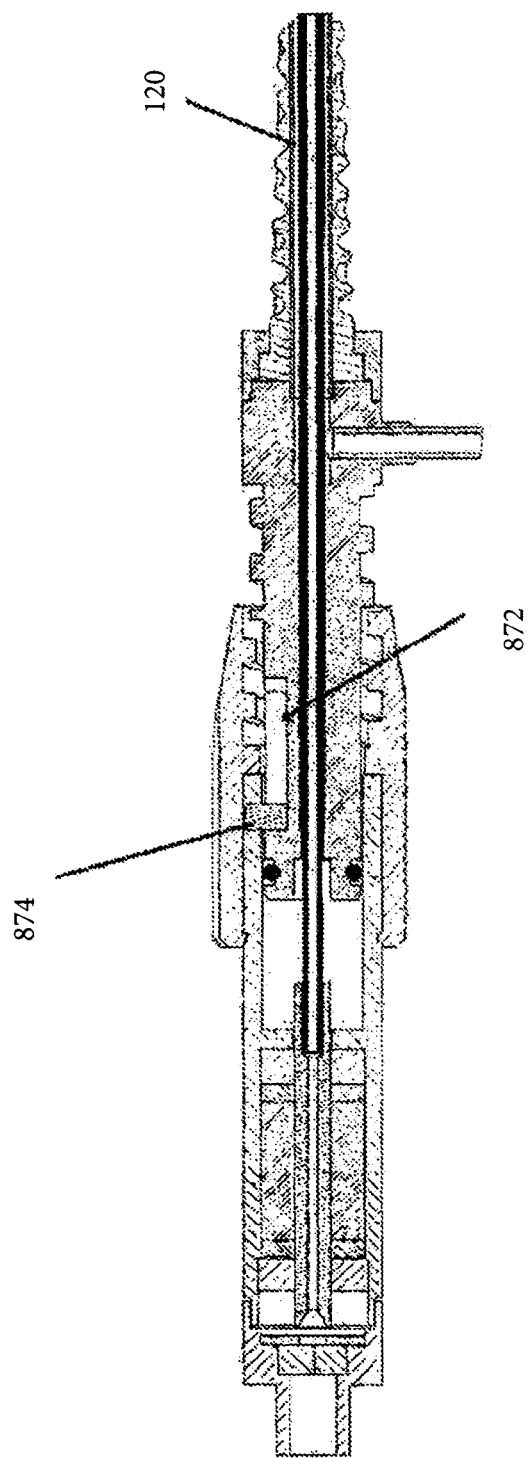

FIGS. 15D-F illustrate another embodiment of a deployment device 850 that can be used to manipulate or deploy a distal structure of the catheter assembly and/or the impeller housing. As with the deployment device 800, the deployment device 850 can be used to actuate the impeller 200 between retracted and deployed configurations.

As discussed above, the catheter assembly can include a flow diverter 852 that is part of the infusion system. The flow diverter 852 may be coupled with a proximal portion 122 of the catheter body 120. In one embodiment, the proximal end of the proximal portion 122 is inserted into a recess 854 formed at a distal 852a end of the flow diverter 852. The connection between the proximal portion 122 of the catheter body 120 the flow diverter 852 can be further made secure by a strain relief 856 disposed at the junction and extending distally thereof. The strain relief 856 overlaps a proximal length of the proximal portion 122 and absorbs movements of the portions of the catheter assembly to isolate the connection between the flow diverter 852 and the catheter body. A cap 860 can be used to securely couple strain relief 856 to the flow diverter 852. A proximal portion 862 of the flow diverter 852 is received within a recess 864 of the housing 450. A seal device 866, such as an O-ring, may be provided between the proximal portion 862 of the flow diverter 852 and inside surface of the recess 864 to prevent infusion from exiting the housing 450 in an undesirable manner.

The flow diverter 852 also includes a lumen 868 that extends from a proximal end 852b to the distal end 852a thereof. The lumen 868 is configured to permit a proximal portion of the drive shaft 148 to reside therein. In some embodiments, flow diverter 852 is configured to cause some infusant to flow proximally in the lumen 868 between the drive shaft 148 and the inner surface of the flow diverter 852 that forms the lumen 868 to lubricate and cool the drive shaft. The flow diverter 852 can be configured to cause most or substantially all of the infusant entering the diverter through the lumen in the catheter body 154 to flow distally between the catheter body 120 and the drive shaft 148. In one arrangement, the lumen 868 is enlarged from a location proximal of where the catheter body 154 couples with the flow diverter 852 toward the distal end 852a of the flow diverter. This enlargement creates a path of least resistance toward the distal direction to divert the flow distally. In one embodiment, the lumen 868 is further enlarged at a location between where the catheter body 154 couples with the flow diverter 852 and the recess 854 such that a substantially continuous lumen can be formed to keep flow resistance at the junction between the flow diverter 852 and the proximal portion 122 of the catheter body 120 to a minimum.

The deployment device 850 includes a guide track 872 on a proximal portion 862 of the flow diverter 852, a guide member 874, and an actuator 876. The guide track 872 can comprise an axially oriented slot or recess formed in the outside surface of the proximal portion 862. The guide track 872 may be configured to slidably receive a guide member 874 such that relative movement can be provided between the guide track 872 and a guide member 874. A portion of the guide member 874 may extend through sidewall of the drive housing 450 such that the axial position of the guide member 874 can be fixed and relative movement is provided by movement of the flow diverter 852 relative to the guide member. In one embodiment the guide member 874 is a pin that has one end received in a small hole in the drive housing 450 and the other end disposed in the guide track 872.

The actuator 876 is configured to translate rotational motion thereof into axial motion of the flow diverter 852. For example, the actuator 876 can comprise a nut that includes internal threads that are engaged with external threads on the outside surface of the flow diverter 852. In various embodiments, a proximal portion of the actuator 876 is anchored to the drive housing 450 to prevent the actuator 876 from moving axially along the drive housing. In one embodiment a retention structure 882 is provided between the actuator 876 and the drive housing 450. One embodiment of the retention structure 882 is illustrated in detail B of FIG. 15D. In particular, the retention structure 882 includes an inwardly protruding member 884 that is received in an annular recess formed in the outside surface of the drive housing 450. The protruding member 890 can include an inwardly protruding ring having n diameter that is less than the diameter of the actuator 876 distally and proximally of the protruding member 884.

FIGS. 15E-F illustrate operation of the deployment device. FIG. 15E corresponds to an expanded configuration of the catheter assembly 100. In this position, the pin 874 is positioned at the distal end of the guide track 872 and the flow diverter 852 is in a proximal position. Because the flow diverter 852, the catheter body 120, and the impeller housing are coupled together so that they move in unison, the catheter body 120 and the impeller housing are also positioned in a relatively proximal position. Relative axial movement is permitted between the impeller and the catheter body, as well as between the diffuser and the catheter body. Also, because the catheter body 120, the flow diverter 852, and the impeller housing move in unison, relative axial movement is permitted between the impeller (and/or diffuser) and the impeller housing. As a result, the impeller will be in a more distal position relative to the impeller housing when the catheter assembly 100 is in the configuration of FIG. 15E. The more distal position moves the impeller into the largest volume portion of the impeller housing enabling the impeller to expand.

FIG. 15F corresponds to a collapsed configuration of the catheter assembly 100. In this position, the pin 874 is positioned at the proximal end of the guide track 872 and the flow diverter 852 is in a distal position. This causes the impeller to be in a more proximal position relative to the housing when the catheter assembly is in the configuration of FIG. 15F. This more proximal position moves the impeller into engagement with the inside surface of the housing tending to collapse the impeller.

To move from the expanded configuration of FIG. 15E to the collapsed configuration of FIG. 15F, the actuator 876 is rotated in a manner that causes the threads to act upon each other which creates axial movement of the catheter body 120 and the impeller housing 202.

C. Catheter Pumps with Adjustable Outflow

It can be important to provide an adequate flow of blood through the catheter pump, e.g., through outlets of the impeller housing. For example, during a treatment procedure, it can be important to pump blood at a sufficiently high flow rate to support the patient's heart pumping. It may be desirable to enable the clinician to adjust (e.g., increase or decrease) the average flow rate through the pump during a procedure by allowing the clinician to adjust the effective area of the outlets, e.g., the area of the outlets that are open and exposed to the flow of blood. In general the flow rate through the pump can be adjusted by adjusting the speed of the motor driving the impeller. In some arrangements, it can be advantageous to provide a mechanism to adjust flow by means other than speed adjustment. In theory a higher rotational speed of the impeller generally leads to a higher hemolysis rate. Thus, it may be advantageous to enable higher average flow rates over a period of time without increasing the impeller rotational speed. In some embodiments, the effective area of the outlets is adjustable during a treatment procedure to modulate or adjust the flow rate of blood through the pump. By adjusting flow rate at the outlets, the risk of hemolysis can be reduced. Furthermore, adjusting flow rate at the outlets (whether or not combined with motor speed adjustments) can enable the clinician to fine tune the flow rate to a sufficiently precise degree.

In some embodiments, it can be advantageous to provide an impeller and impeller housing that are configured to provide an adjustable outflow, e.g., to adjust the amount of blood that flows out of the impeller housing through the outlets. For example, the impeller housing can comprise a cannula having one or more outlets near a proximal portion of the impeller.

It has been found that the flow performance (flow rate, hemolysis rate, etc.) can vary along the length of the cannula. For example, if the impeller is positioned too close to the outlets or inlets, swirls and turbulence can result which diminish flow rate and increase hemolysis. Similarly, it has been found that performance can vary even along the middle portion of the cannula. In fact, the ideal location may depend on many factors such as rotational speed, patient physiology, and more. The flow pattern can be based on hysteresis. Accordingly, it may be advantageous to enable the impeller to move relative to the cannula. As will be appreciated from the description above, the inner wall of the cannula acts as a shroud around the impeller. In various embodiments, the catheter pump is configured so the impeller can move relative to the cannula during operation, and in some respects, relative to the outlets. In one embodiment, the catheter pump can be configured to provide relative axial movement between the cannula and the impeller to position the outlets at a desired position relative to the impeller. The clinician can therefore move the impeller housing and outlets axially relative to the impeller, or vice versa, to adjust the flow of blood through the outlets. This allows the clinician to "dial in" the performance during operation. Using measurement tools like the flow rate indicator, the physician and move the impeller back and forth until the desired parameter or parameters are optimized.

In various embodiments, a sleeve can be disposed about the cannula and outlets. The sleeve can be configured to slide relative to the cannula to selectively occlude and/or expose the outlets. For example, in a fully open configuration, the sleeve can be positioned away from the outlets such that the outlets are full open and exposed to the flow of blood. In a fully closed configuration, the sleeve can be positioned over the outlets to substantially fully occlude the outlets. In the closed configuration, the sleeve can prevent blood from flowing through the outlets. In intermediate configurations, the sleeve can partially occlude the outlets to provide a flow rate less than the flow rate in the open configuration. The clinician can adjust the amount by which the outlets are occluded to adjust the flow rate through the pump. In some embodiments, the sleeve extends distally from the outlets towards the distal end of the catheter pump. In such embodiments, longitudinal filaments can extend proximally from the sleeve to the proximal end of the catheter pump. The clinician can pull the filaments towards the proximal end of the catheter pump to occlude the outlets and can push the filaments distally towards the distal end of the catheter pump to expose the outlets. In other embodiments, the sleeve extends proximally from the outlets towards the proximal end of the catheter pump. In such embodiments, the clinician can push the sleeve distally to occlude the outlets and can pull the sleeve proximally to expose the outlets.

Figure 16B:
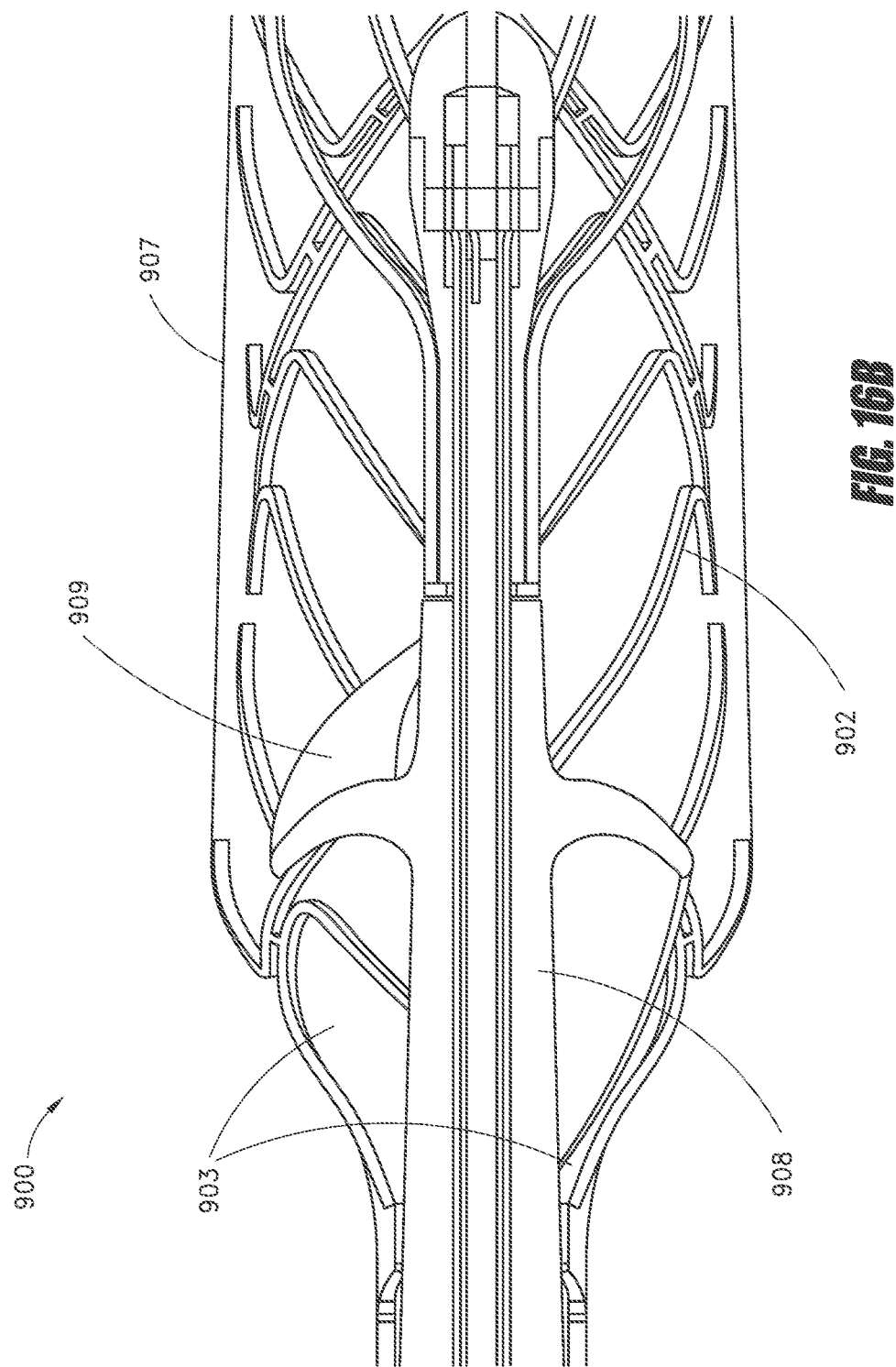

FIGS. 16A-16B are side cross-sectional views of a catheter pump 900 having a cannula 902 and an impeller 908 disposed within the cannula 902, according to some embodiments. The cannula 902 can comprise a mesh (which may comprise nitinol) and an elastic coating 907 disposed about the mesh. The elastic coating 907 can enclose openings in the mesh to form a flow duct through which blood can flow. One or more outlets 903 can be disposed at a proximal portion of the cannula 902. The outlets 903 can comprise openings in the cannula 902, e.g., portions of the cannula 902 that are not covered by the elastic coating 907.

In the arrangement of FIGS. 16A-16B, the pump 900 is configured such that relative motion can be provided between the impeller 908 and the cannula 902. For example, in some embodiments, the impeller 908 can be displaced axially in a distal direction (+x direction) and/or a proximal direction (−x direction) relative to the cannula 902. In other embodiments, the cannula 902 can be displaced axially in the distal direction (+x direction) and/or the proximal direction (−x direction) relative to the impeller 908. By providing relative motion between the impeller 908 and the cannula 902, the flow rate of blood passing through the outlets 903 can be adjusted. For example, the clinician can move the impeller 908 or cannula 902 to achieve a flow rate sufficiently high to support the heart during a treatment procedure.

For example, in FIG. 16A, the impeller 908 is positioned at a distal location relative to the cannula 902. The impeller 908 can include one or more blades. In the distal location of FIG. 16A, a proximal blade 909 of the impeller may be offset from the outlets 903 axially. When the impeller 908 rotates, blood can be drawn proximally in the −x direction and can pass through the outlets 903. In some arrangements, the clinician may desire to increase the flow rate through the pump 900. In the embodiment of FIGS. 16A-16B, the clinician may provide relative motion between the impeller 908 and cannula 902 to reposition the impeller 908 relative to the cannula 902, or vice versa. For example, in FIG. 16B, sufficient relative motion may be applied to the cannula 902 or impeller 908 to position the impeller 908 at a proximal location relative to the cannula 902. In the proximal location of FIG. 16B, the proximal blade 909 of the impeller 908 can be positioned nearer the outlets 903 relative to the distal location of FIG. 16A. By positioning the proximal blade 909 near the outlets 903, the proximal blade 909 can direct the flow of blood through the outlets 903 in an efficient manner to increase the flow rate through the pump 900. In particular, when the proximal blade 909 (or a proximal portion of the impeller) is disposed at or near the outlets 903, the proximal blade 909 (or proximal portion of the impeller) can act as a flow channel to guide the blood proximally through the outlets 903 with reduced losses.

Relative motion between the cannula 902 and impeller 908 can be provided in any suitable manner. For example, the impeller 908 can be moved distally and/or proximally using the mechanisms disclosed herein with respect to FIGS. 14A-14B and 15A-15F. In other embodiments, a pull wire, a filament, or other mechanism can be configured to move the impeller 908 and/or the cannula 902. Still other translation mechanisms may be suitable.

FIG. 17 is a side cross-sectional view of a catheter pump 900, according to another embodiment. As with the embodiment of FIGS. 16A-16B, the catheter pump 900 can include a cannula 902 having a mesh and an elastic coating 907 disposed about the mesh. An impeller 908 having at least one blade (e.g., a proximal blade 909) can be disposed in the cannula 902. One or more outlets 903 can be provided through a proximal portion of the cannula 902. In the embodiment of FIG. 17, the catheter pump 900 may or may not be configured such that relative motion can be provided between the impeller 908 and the cannula 902. To adjust the flow rate of blood flowing out through the outlets 903, a sleeve 911 can be disposed about an outer surface of the cannula 902. The sleeve 911 can comprise any suitable material, such as an elastic or plastic tube. The sleeve 911 may be biased to conform to the cannula 902 in some arrangements. The sleeve 911 can be moved in any suitable manner, such as by the clinician pulling tensile elements (such as wires) or filaments 995 coupled to the sleeve.

The catheter pump 900 can be configured such that the sleeve 911 can move axially in the +x and −x directions relative to the cannula 902 by manipulating the filaments 995. For example, the sleeve 911 can comprise a proximal end 913. When the sleeve 911 is axially translated relative to the cannula 902 (or vice versa) (e.g., pulled proximally with the filaments 995), the proximal end 913 can occlude a portion of the area of the outlets 903, thereby defining an effective area for the outlets 903. For example, the sleeve 911 can be configured to occlude the outlets 903 entirely within Zone A illustrated in FIG. 17. When the proximal end 913 is disposed within Zone A, the sleeve 911 occludes the entire area of the outlets 903 such that no blood flows through the outlets 903. At a fully open position, the proximal end 913 may be disposed within Zone C. In such a fully open position, the outlets 903 may not be occluded at all, which may provide a high flow rate through the pump 900. At an intermediate position, the proximal end 913 may be disposed within Zone B to partially occlude the outlets 903.

Although the embodiment illustrated in FIG. 17 includes a sleeve with a proximal end that is moveable over the outlets, in other arrangements, a sleeve may be disposed proximal the outlets 903 such that a distal end of the sleeve is moveable over the cannula 902 to occlude the outlets 903. Thus, in other arrangements, the sleeve 911 can instead extend proximally from the outlets 903 towards the proximal end of the catheter pump 900. In such embodiments, the clinician can push the sleeve 911 to move the sleeve 911 distally and can pull the sleeve 911 to move the sleeve proximally relative to the outlets 903. The sleeves described herein can act to change the effective area of the outlets to adjust the flow of blood from the cannula. For example, the clinician can push the sleeve (which may be the same as or different from a sheath used to collapse the cannula) over the outlets 903 to adjust flow.

The clinician can provide relative motion between the sleeve 911 and the cannula 902 to achieve a desired flow rate through the pump. For example, if the clinician wants to decrease the flow rate for the sleeve arrangement shown in FIG. 17, the clinician may move the proximal end 913 of the sleeve to an intermediate partially occluded position within Zone B (e.g., by pulling the sleeve 911 proximally using the filaments 995). If the clinician wants to increase the flow rate, the clinician can move the proximal end 913 of the sleeve 911 further distally (e.g., by pushing the sleeve 911 proximally using the filaments 995). The catheter pump 900 can be calibrated such that the clinician can achieve accurate flow rates by precise positioning of the sleeve 911 relative to the cannula 902. For example, hash marks or other markings may be measured at a proximal end portion of the pump 900 outside the patient's body. The hash marks can represent the position of the sleeve 911 relative to the cannula 902, and each hash mark can correspond to an estimated flow rate. Accordingly, in the embodiment, of FIG. 17, the clinician can adjust the effective area of the outlets exposed to the flow of blood to suitably adjust the flow rate.

In some embodiments, the cannula 902 can be actuated by supplying an electric current to the metal (e.g., nitinol) that forms the mesh of the cannula 902. The material forming the cannula 902 can be manufactured to have an expanded state in an austenitic phase (e.g., when heated) or a contracted state in the austenitic phase. Accordingly, in some embodiments, electric current can pass through a nitinol mesh of the cannula 902, which can heat the material forming the cannula 902. The current can be increased or decreased to cause the metal to contract or expand. The pump can be sufficiently calibrated such that the electric current can controllably cause the mesh to elongate or shorten. For example, in some embodiments, sufficient electric current can be supplied to the cannula 902 to cause the cannula to move relative to the impeller 908 and/or sleeve 911. In some embodiments, sufficient electrical current can be supplied to cause the outlets 903 of the cannula 902 to contract or expand, thereby changing the effective area of the outlets 903 exposed to the flow of blood to control the flow rate of blood flowing therethrough.

IV. Methods

Various methods and techniques are discussed above in connection with specific structures of heart pumps. The following elaborates on some aspects of these techniques and methods. The following discussion is to be read in light of and freely combined with the foregoing discussion.

As discussed above, in various embodiments the heart pump 10 is inserted in a less invasive manner, e.g., using techniques that can be employed in a catheter lab. Various general techniques pertinent to the heart pump 10 are described in U.S. patent application Ser. No. 12/829,359, filed on Jul. 1, 2010, and entitled *Blood Pump With Expandable Cannula*, which is incorporated by reference herein in its entirety and for all purposes.

Because the catheter assembly 100 is to be delivered through a small access site, it can be important to ensure that the impeller housing is reliably deployed and retracted, as described above. A clinician may begin a heart pumping procedure by introducing the catheter assembly 100 into the patient percutaneously, e.g., by urging the catheter assembly through the femoral artery and into a heart chamber. Because the impeller and impeller housing are advanced through a narrow artery in some embodiments, the impeller and impeller housing can initially be inserted into the patient in a retracted, or collapsed (or low profile), state, as described above. Once the distal end of the catheter assembly 100 (including the impeller housing) has reached the desired operating location (e.g., a heart chamber), the clinician can deploy the impeller housing into an advanced or expanded configuration.

One method of deploying the impeller and/or diffuser is by using the impeller deployment assembly 800, which can be located near the proximal end of the catheter assembly. As shown in FIGS. 15A and 15B, the clinician can rotate the nut 804 (clockwise or counter-clockwise depending on the threading) such that the nut 804 translates from a distal position to a proximal position. In turn, the flow diverter 806, the catheter body, and the impeller housing can also translate from a distal position to a proximal position and thereby advance the impeller distally into a wider portion of the impeller housing to allow for deployment of the impeller hub 208 and blades 212. Thus, in some embodiments, the clinician can deploy the impeller, located at a distal end of the catheter assembly, by rotating a nut disposed near the proximal end of the catheter assembly.

In some embodiments, the impeller 200 and housing 202 can be axially displaced relative to their operational positions during delivery of the distal end to the heart (e.g., the impeller and housing can be delivered to the vasculature in an axially separated configuration). As used in this context, "axially displaced" includes configurations where there is axial movement of the impeller 200 relative to any portion of the housing 202 prior to or during the process of delivery. For example, axial displacement includes conditions in which the impeller 200 is moved from a first position near a proximal end port (outlet for left side support or inlet for right side support) of the housing 202 to a second position distal the first position. The second position can be one that is still between the proximal end port and a distal end port (inlet for left side support or outlet for right side support) of the housing 202. The first position may be the operational position of the impeller 200 relative to the housing 202. Axial displacement also includes conditions in which the impeller is located proximal of an operational position, e.g., at a location proximal of a proximal end port of the housing 202, including being disposed within a non-expandable portion of the heart pump. When the clinician delivers the distal end of the heart pump to the heart chamber, rather than delivering the distal end with the impeller housing disposed over the impeller blades, the impeller housing can be in a proximally displaced position or retracted configuration (or distally displaced position or advanced configuration in other embodiments) with respect to the impeller, such that it is axially moved from the operational position, as discussed above.

In some embodiments, the impeller and the housing can be delivered in series (with the impeller being delivered before the housing, or vice versa). For example, in one embodiment, the impeller housing 202 is first advanced into position, e.g., in the heart. The housing 202 may then be expanded if the housing has expanded and compressed configurations. Thereafter the impeller 200 may be positioned, e.g., advanced through a catheter body similar to the catheter body 120 to be positioned within the impeller housing 202. Thereafter the impeller 200 can be rotated by a source of rotational energy. In various embodiments, the source of rotational energy can comprise a motor positioned outside of the patient to drive a shaft similar to the shaft 148. In other embodiment, the source of rotational energy can comprise a motor that is miniaturized to be positionable within the patient, as discussed in U.S. Pat. No. 7,070,555, which is incorporated by reference herein for all purposes and in its entirety. In another embodiment, the distal end of the impeller 200 can be configured to be advanced into position in the patient and, at a later stage of a procedure, the impeller housing 202 can be positioned thereover. In one technique, the impeller 200 is positioned in the heart chamber (or wherever the procedure is to occur), the clinician can then advance the impeller housing over the impeller blades and begin operating the heart pump. For removal of the catheter assembly from the patient after the procedure, the clinician can retract or displace the impeller housing proximally to axially displace and/or separate the impeller from the impeller housing.

The configurations enabling displaced or serial delivery also can decouple the design of the impeller housing 202 from the complexities of the design of the impeller 200. For example, the impeller housing 202 can have a greater range of expansion from a collapsed state to an expanded state. If no structures are disposed inside the housing 202 in the collapsed state, greater compression and a lower crossing profile can be achieved compared to where the housing 202 must be sized in the collapsed state to accommodate the impeller 200 in its collapsed state. This provides one or more of the benefits of access through smaller vessels, in smaller patients, or a larger expanded size in standard patients through typical access (e.g., femoral vessel). Similarly, greater compression of the impeller 200 may be possible if the impeller 200 is delivered using a dedicated compression sheath or device that is not required to expand and/or to be present around the impeller during operation. As a result, larger blades may be delivered from the same collapsed profile, providing the advantages of higher flow discussed above. More details of serial delivery of blood pumps are discussed in U.S. Pat. No. 7,022,100, which is incorporated by reference herein for all purposes and in its entirety.

Once the impeller is deployed, the clinician can conduct the procedure, e.g., by running the heart pump within a heart chamber. Once the procedure is finished, the clinician can remove the catheter assembly from the patient by retracting the impeller. The clinician can simply rotate the nut 804 in a direction opposite to that rotated for deploying the impeller. The nut can then translate from the proximal position to the distal position, which in turn can cause the flow diverter 806, the catheter body, and the impeller housing to also translate from the proximal position to the distal position. The impeller can thereby be retracted proximally into an area near the outlet 802 to reduce the profile of the pump upon collapsing into the sheath. Thus, the clinician can both deploy and retract the impeller by rotating a nut located near the proximal end of the catheter assembly.

In some embodiments, relative motion can be provided between the impeller and the cannula to achieve a desired flow rate. For example, the impeller or the cannula can be moved axially to position the outlets at a desired position relative to the impeller. In some embodiments, the impeller can be positioned such that a proximal blade is near the outlets. Disposing the proximal blade near the outlets can act to direct the flow of blood through the outlets. In other embodiments, a sleeve can be disposed over the cannula. The sleeve can be translated axially relative to the cannula to expose a desired effective area of the outlets. For example, the clinician can move the sleeve to partially occlude the outlets to achieve a desired flow rate.

In some embodiments, a cannula and an impeller within the cannula can be advanced to a target location in a patient. The heart pump can be activated to rotate the impeller to pump blood through the cannula along a longitudinal axis. Relative motion can be provided between the impeller and the cannula along the longitudinal axis while the impeller is rotating. The relative motion can be provided in any suitable manner explained above, including, e.g., the embodiments disclosed in FIGS. 14A-14B and 15A-15F. As explained herein, providing relative motion between the impeller and the cannula can improve an average flow rate of blood that flows through the cannula, which can improve patient outcomes.

In some arrangements, one or more sensors can measure a parameter associated with the flow of blood through the cannula. For example, the sensor(s) can measure an average flow rate of blood that is pumped through the cannula, e.g., directly or indirectly based on a pressure differential. A processor can be programmed to receive and process the data detected by the sensor(s). For example, the processor can process the raw sensor data to estimate an average flow rate over a predetermined period of time. The processor can also be programmed to send a signal to a user interface to notify the clinician regarding the detected parameter (e.g., flow rate, pressure, etc.).

Relative motion can be provided such that the impeller moves proximally or distally relative to the cannula based at least in part on the parameters measured by the sensor(s) and processed by the processor. The heart pump can be configured to adjust the outflow of blood through the cannula by enabling the clinician to move the impeller relative to the cannula (or vice versa) if the flow rate is insufficient. For example, if the sensor(s) indicates that the flow rate is too low, then the clinician may move the impeller proximally relative to the cannula. The sensor(s) can provide an updated estimate of flow rate to the clinician. If the updated flow rate parameter is sufficiently or preferentially improved, the clinician may elect to maintain the relative position of the impeller and cannula. If, however, the updated flow rate parameter does not improve, or does not improve by a sufficient amount, then the clinician may elect to provide additional relative movement between the impeller and cannula.

In some embodiments, a cannula and an impeller can be advanced to a target location in a patient. The impeller can be positioned in the cannula, and the cannula can comprise one or more outlets. The heart pump can be activated to rotate the impeller to pump blood through the cannula along a longitudinal axis. An effective area of the outlets can be adjusted while the impeller is rotating. Adjusting the effective area of the outlets can advantageously change an average flow rate of blood through the cannula over a time period during a treatment procedure. As explained above, an end of a sleeve can be advanced over the outlets to at least partially occlude the outlets to change the effective area of the outlets. The sleeve can also partially occlude the outlets in some arrangements.

As above, one or more sensor(s) can detect a parameter of the pumped blood (e.g., flow rate, pressure, etc.). A processor can process the signal detected by the sensor(s) to convert the signal into data representative of the parameter. The processor can notify the clinician regarding the parameter. As above, the clinician can change the effective area of the outlets in response to the measured parameter. For example, if the flow rate is too low, the clinician may move the sleeve away from the outlets to increase the effective area of the outlets. The clinician can view the updated measurements on a user interface. If the flow rate is still too low, the clinician can provide additional movement to the sleeve. If the flow rate is sufficient, the clinician can maintain the sleeve at its current relative position.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A heart pump comprising:
   a cannula having one or more outlets;
   an impeller positioned in the cannula, the impeller comprising a shaft on which the impeller is mounted and a rotating hub configured to pump blood through the outlets along a longitudinal axis when the impeller is rotated at an operational speed; and
   a diffuser positioned in the cannula adjacent the one or more outlets and adjacent a proximate end of the hub, wherein the diffuser is configured to direct fluid flow through the one or more outlets;
   wherein the heart pump is configured to adjust a flow rate through the one or more outlets by providing relative motion between the cannula and the impeller along the longitudinal axis while the impeller is rotating, the relative motion between the cannula and the impeller created by moving the shaft longitudinally relative to the cannula.

2. The heart pump of claim 1, wherein the diffuser is coupled to hub such that the diffuser rotates with the hub.

3. The heart pump of claim 2, wherein the diffuser is integrally formed as a unitary piece with the hub.

4. The heart pump of claim 1, wherein the diffuser is spaced from the proximate end of the hub such that the diffuser is stationary during rotation of the hub.

5. The heart pump of claim 4, wherein the diffuser includes a distal outlet positioned adjacent the proximate end of the hub.

6. The heart pump of claim 1, wherein diffuser includes:
a distal end positioned adjacent the proximate end of the hub; and
a proximate end positioned adjacent a distal end of a bearing housing of the heart pump.

7. The heart pump of claim 6, wherein diffuser includes a proximate outlet positioned adjacent the bearing housing.

8. The heart pump of claim 6, wherein diffuser includes a wall comprising an outer surface that is curved from the distal end to the proximate end, wherein the wall is configured to direct fluid flow.

9. The heart pump of claim 6, wherein the diffuser includes a first diameter at a diffuser midsection and a second diameter at the distal end and the proximate end, wherein the diffuser tapers to the second diameter from the midsection.

10. The heart pump of claim 1, wherein the diffuser is formed from a flexible material to enable movement between a collapsed configuration and an expanded configuration.

11. The heart pump of claim 10, wherein the diffuser includes a maximum diameter in the expanded configuration that is larger than a diameter of the hub, and wherein the diffuser includes a maximum diameter in the collapsed configuration that is less than or equal to a diameter of the hub.

12. The heart pump of claim 1, wherein diffuser includes a curved wall that forms an inner chamber that at least partially defines a fluid path, wherein the fluid is configured to travel in a distal direction along the fluid path within the inner chamber.

13. The heart pump of claim 12, wherein the fluid path extends from a proximate end of the diffuser to a distal end of the diffuser along a helical route around a shaft extending through the inner chamber.

14. A method of operating a heart pump, the method comprising:
advancing a cannula and an impeller to a target location in a patient, the impeller being positioned in the cannula;
activating the heart pump to rotate the impeller to pump blood through the cannula along a longitudinal axis toward one or more outlets of the cannula, the impeller comprising a shaft on which the impeller is mounted and a rotating hub; and
directing the blood through the one or more outlets using a diffuser positioned in the cannula adjacent the one or more outlets and adjacent a proximate end of the hub; and
providing relative motion between the impeller and the cannula along the longitudinal axis while the impeller is rotating, the relative motion between the cannula and the impeller created by moving the shaft longitudinally relative to the cannula.

15. The method of claim 14, wherein directing the blood comprises directing the blood along an outer surface of a wall of the diffuser, wherein the outer surface is curved from a diffuser distal end to a diffuser proximate end.

16. The method of claim 15, further comprising directing an infusant flow along an infusant flow fluid path within an inner chamber at least partially defined by an inner surface of the wall, wherein the infusant flow is configured to travel in a distal direction along the infusant flow path within the inner chamber.

17. The method of claim 16, wherein directing the infusant flow comprises directing the infusant flow from a proximate end of the diffuser to a distal end of the diffuser along a helical route around a shaft extending through the inner chamber.

18. The method of claim 17, wherein directing the infusant flow comprises directing the infusant flow toward a distal outlet of the diffuser.

19. The method of claim 17, wherein directing the infusant flow comprises directing the infusant flow from the distal end of the diffuser toward the proximate end of the diffuser in a non-helical route along the inner surface of the wall, and wherein the fluid exits the diffuser at a proximate diffuser outlet.

20. The method of claim 14, wherein directing the blood comprises moving the diffuser between a collapsed configuration and an expanded configuration, wherein the diffuser includes a maximum diameter in the expanded configuration that is larger than a diameter of the hub, and wherein the diffuser includes a maximum diameter in the expanded configuration that is larger than a diameter of the hub.

* * * * *